US006258565B1

(12) United States Patent
Blatny et al.

(10) Patent No.: US 6,258,565 B1
(45) Date of Patent: Jul. 10, 2001

(54) EXPRESSION VECTORS BASED ON RK2 AND TOL PLASMIDS

(75) Inventors: Janet M. Blatny; Ponniah Karunakaran; Svein Valla, all of Trondheim (NO)

(73) Assignee: Leiv Eiriksson Nyfotek AS, Trondheim (NO)

( * ) Notice: Subject to any disclaimer, the term of this patent is extended or adjusted under 35 U.S.C. 154(b) by 0 days.

(21) Appl. No.: 09/242,945

(22) PCT Filed: Aug. 28, 1997

(86) PCT No.: PCT/GB97/02323

§ 371 Date: Sep. 10, 1999

§ 102(e) Date: Sep. 10, 1999

(87) PCT Pub. No.: WO98/08958

PCT Pub. Date: Mar. 5, 1998

(30) Foreign Application Priority Data

Aug. 29, 1996 (GB) .................................................. 9618001

(51) Int. Cl.[7] .............................. C12P 21/04; C12N 1/12; C12N 15/63; C12N 15/00; C07H 21/04

(52) U.S. Cl. .................. 435/71.2; 435/252.1; 435/320.1; 435/440; 536/23.1; 536/24.1

(58) Field of Search ............................... 435/71.2, 252.1, 435/320.1, 440; 536/23.1, 24.1

(56) References Cited

FOREIGN PATENT DOCUMENTS

| 0443063 A1 | 8/1991 | (EP) . |
| 89/09823 | 10/1989 | (WO) . |
| 91/16439 | 10/1991 | (WO) . |
| 96/08572 | 3/1996 | (WO) . |

OTHER PUBLICATIONS

Assinder, S.J., et al., "The TOL Plasmids: Determinants of the Catabolism of Toluene and the Xylenes", *Advances in Microbial Physiology*, vol. 31, 1–69, (1990).

Blatny, J.M., et al., "Construction and Use of a Versatile Set of Broad–Host–Range Cloning and Expression Vectors Based on the RK2 Replicon", *Applied and Environmental Microbiology*, vol. 63, No. 2, 370–379, (Feb. 1997).

Blatny, J.M., et al., "Improved Broad–Host–range RK2 Vectors Useful for High and Low Regulated Gene Expression Levels in Gram–Negative Bacteria", *Plasmid*, vol. 38, 35–51, (1997).

Calero, S., et al., "Expression of the Meta–Cleavage Pathway Operon of the TOL Plasmid of *Pseudomonas putida* in the phototropic bacterium *Rhodobacter sphaeroides*", *Journal of Biotechnology*, vol. 12, 231–246, (1989).

Chakrabarty, A.M., et al., "Transposition of Plasmid DNA Segments Specifying Hydrocarabon Degradation and their Expression in Various Microogranisms", *Proc. Nat'l. Acad. Sci. USA*, vol. 75, No. 7, 3109–3112, (Jul. 1978).

Ditta, G., et al., "Plasmids Related to the Broad Host Range Vector, pRK290, Useful for Gene Cloning and for Monitoring Gene Expression", *Plasmid*, vol. 13, 149–153, (1985).

Dixon, R., "The xylABC Promoter from the *Pseudomonas putida* TOL Plasmid is Activated by Nitrogen Regulatory Genes in *Escherichia coli*", *Mol Gen Genet*, vol. 203, 129–136, (1986).

Durland, R.H., et al., "Mutations in the trfA Replication Gene of the Broad–Host–Range Plasmid RK2 Result in Elevated Plasmid Copy Numbers", *Journal of Bacteriology*, vol. 172, No. 7, 3569–3867, (Jul. 1990).

Figurski, D.H., et al., "Suppression of ColE1 Replication Properties by the Inc P–1 Plasmid RK2 in Hybrid Plasmids Constructed in Vitro", *J. Mol. Biol.*, vol. 133, 295–318, (1979).

Franklin, F.C., et al., "Chapter 10—Broad–Host–Range Cloning Vectors", *Promiscuous Plasmids of Gram–Negative Bacteria, Copyright 1989, Acaademic Press Limited,*, ISBN 0–12–688480–3, 247–267 (1989).

Guiney, D.G., et al., "Chapter 2—Conjugative Transfer of IncP Plasmids", *Promiscuous Plasmids of Gram–Negative Bacteria, Copyright 1989, Academic Press Limited*, ISBN 0–12–688480–3, 27–56, (1989).

Harayama, S., et al., "Characterization of Five Genes in the Upper–Pathway Operon of TOL Plasmid pWW0 from*Pseudomonas putida* and Identification of the Gene Products", *Journal of Bacteriology*, vol. 171, No. 9, 5048–5055, (1989).

Haugan, K., et al., "The Host Range of RK3 Minimal Replicon Copy–Up Mutants is Limited by Species–Specific Differences in the Maximum Tolerable Copy Number", *Plasmid*, vol. 33, 27–39, (1995).

Haugan, K., et al., "The Phenotypes of Temperature–Sensitive Mini–RK2 Replicons Carrying Mutations in the Replication Control Gene trfA are Suppressed Nonspecifically by Intragenic cop Mutations", *Journal of Bacteriology*, vol. 174, No. 21, 7026–7032, (Nov. 1992).

Ingram, L.C., "Molecular Characterization of the R Factors Implicated in the Carbenicilllin Resistance of a Sequence of *Pseudomonas aeruginosa* Strains Isolated from Burns", *Antimicrobial Agents and Chemotherapy*, vol. 3, No. 2, 279–288, (Feb. 1973).

(List continued on next page.)

*Primary Examiner*—Robert A. Schwartzman
*Assistant Examiner*—William Sandals
(74) *Attorney, Agent, or Firm*—Schwegman, Lundberg, Woessner & Kluth, P.A.

(57) ABSTRACT

The present invention provides an expression vector comprising an RK2 minimum replicon together with an expression cassette comprising the regulatory functions of a TOL plasmid, and, in particular, an expression vector comprising a RK2 minimum replicon together with a promoter Pm and/or Pu and a corresponding regulatory gene xylS and/or xylR as derived from a TOL plasmid. Such expression vectors may be used to express desired genes in a wide range of gram negative and gram positive bacterial hosts.

15 Claims, 12 Drawing Sheets

OTHER PUBLICATIONS

Figure 1A:
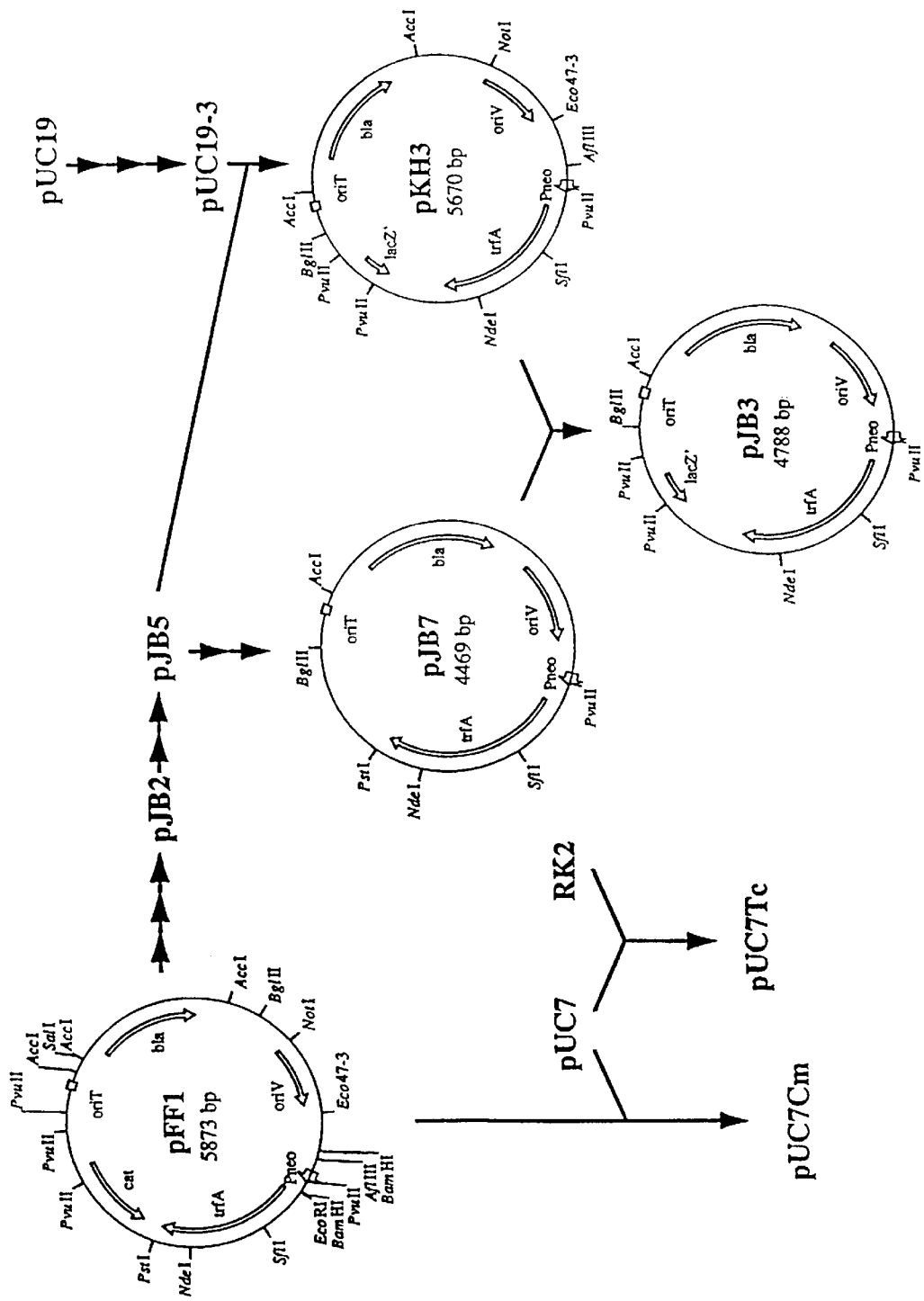

Inouye, S., et al., "Molecular Cloning of Regulatory Gene xylR and Operator–Promoter Regions of the xylABC and xylDEFG Operons of the TOL Plasmid", *Journal of Bacteriology*, vol. 155, No. 3, 1192–1199, (Sep. 1983).

Inouye, S., et al., "Nucleotide Sequence of the Promoter Region of the xylDEGF Operon on TOL Plasmid of *Pseudomonas putida*", *Genes*, vol. 29, 323–330, (1984).

Keil, H., et al., "Molecular Analysis of Regulatory and Structural xyl Genes of the TOL Plasmid pWW53-4", *Journal of General Microbiology*, vol. 133, 1149–1158, (1987).

Keil, S., et al., "Construction of a Cassette Enabling Regulated Gene Expression in the Presence of Aromatic Hydrocarbons", *Plasmid*, vol. 27, 191–199, (1992).

Kessler, B., et al., "Genetic Evidence that the XylS Regulator of the Pseudomonas TOL meta Operon Controls the Pm Promoter Through Weak DNA–Protein Internations", *Journal of Bacteriology*, vol. 176, No. 11, 3171–3176, (Jun. 1994).

Kessler, B., et al., "Identification of a cis–acting Sequence with the Pm Promoter of the TOL Plasmid which Confers XylS–Medicated Responsiveness to Substituted Benzoates", *J. Mol. Biol.*, vol. 230, 699–703, (1993).

Li, X., et al., "Generation of Auxotrophic Mutants of *Enterococcus faecalis*", *Journal of Bacteriology*, vol. 177, No. 23, 6866–6873, (Dec. 1995).

Mermod, N., et al., "Vector for Regulated Expression of Cloned Genes in a Wide Range of Gram–Negative Bacteria", *Journal of Bacteriology*, vol. 167, No. 2, 447–454, (Aug. 1986).

Michan, C., et al., "Identification of Critical Amino–terminal Regions of XylS", *The Journal of Biological Chemistry*, vol. 267, No. 32, 22897–22901, (Nov. 13, 1992).

Morris, C.J., et al., "Identification and Nucleotide Sequences of mxaA, mxaC, mxaK, mxaL, and mxaD Genes from Methylobacterium extorquens AM1", *Journal of Bacteriology*, vol. 177, No. 2, 527–535, (Feb. 1978).

Nakazawa, T., "TOL Plasmid in *Pseudomonas aeruginosa* PAO: Thermosensitivity of Self–Maintenance and Inhibition of Host Cell Growth", *Journal of Bacteriology*, vol. 133, No. 2, 527–535, (Feb. 1978).

Osteras, M., et al., "Molecular and Expression Analysis of the *Rhizobium meliloti* Phosphoenolpyruvate Carboxykinase (pckA) Gene", *Journal of Bacteriology*, vol. 177, 1452–1460, (Mar. 1995).

Pansegrau, W., et al., "Complete Nucleotide Sequence of Birmingham IncPa Plasmids—Compilation and Comparative Analysis", *J. Mol. Biol.*, vol. 239, 623–663, (1994).

Perri, S., et al., "Interactions of Plasmid–encoded Replication Initiation Proteins with the Origin of DNA Replication in the Broad Host Range Plasmid RK2*", *The Journal of Biological Chemistry*, vol. 266, No. 19, 12536–12543, (Jul. 5, 1991).

Ramos, J.L., et al., "Altered Effector Specificities in Regulators of Gene Expression: TOL Plasmid xylS Mutants and their Use to Engineer Expansion of the Range of Aromatics Degraded by Bacteria", *Proc. Natl. Acad. Sci. USA*, vol. 83, 8467–8471, (Nov. 1986).

Ramos, J.L., et al., "Broad–Host–Range Expression Vectors Containing Manipulated meta–Cleavage Pathway Regulatory Elements of the TOL Plasmid", *FEBS Letters 05437*, vol. 226, No. 2, 241–246, (Jan. 1988).

Ramos, J.L., et al., "Signal–Regulator Interactions, Genetic Analysis of the Effector Binding Site of xylS, the Benzoate–activated Positive Regulator of Pseudomonas TOL Plasmid Meta–Cleavage Pathway Operon", *J. Mol. Biol.*, vol. 211, 373–382, (1990).

Roberts, R.C., et al, "Definition of a Minimal Plasmid Stabilization System from the Broad–Host–Range Plasmid RK2", *Journal of Bacteriology*, vol. 174, No. 24, 8119–8132, (Dec. 1992).

Roberts, R.C., et al., "Genetic Characterization of the Stabilizing Functions of a Region of Broad–Host–Range Plasmid RK2", *Journal of Bacteriology*, vol. 172, No. 11, 6204–6216, (Nov. 1990).

Schmidhauser, T.J., et al., "Regions of Broad–Host–Range Plasmid RK2 Involved in Replication and Stable Maitenance in Nine Species of Gram–Negative Bacteria", *Journal of Bacteriology*, vol. 164, No. 1, 446–455, (Oct. 1985).

Shingler, V., et al., "Anaylsis of the trfA Region of Broad Host–Range Plasmid RK2 by Transposon Mutagenesis and Identification of Polypeptide Products", *J. Mol. Biol.*, vol. 175, 229–249, (1984).

Sia, E.A., et al., "Different Relative Importances of the par Operons and the Effect of Conjugal Transfer on the Maintenance of Intact Promiscuous Plasmid RK2", *Journal of Bacteriology*, vol. 177, No. 2, 2789–2797, (May 1995).

Smith, C.A., et al., "Chapter 3—Relationships and Evolution of IncP Plasmids", *Promiscuous Plasmids of Gram–Negative Bacteria*, ISBN 0–12–688480–3, 57–77, (1989).

Thomas, C.M., et al., "Chapter 1—Vegetative Replication and Stable Inheritance of IncP Plasmids", *Promiscuous Plasmids of Gram–Negative Bacteria*, ISBN 0–12–688480–3, 1–25, (1989).

Valla, S., et al., "Isolation and Properties of Temperature–Sensitive Mutants of the trfA Gene of the Host Range Plasmid RK2", *Plasmid*, vol. 25, 131–136, (1991).

EXPRESSION VECTORS BASED ON RK2 AND TOL PLASMIDS

The present invention relates to novel expression vectors for expressing desired genes within a range of bacterial hosts and, in particular, to expression vectors based on the RK2 replicon and the TOL plasmid regulatory functions.

The cloning and expression of genes is a central tool in biotechnology. Traditionally, genes have been cloned and expressed in enteric bacteria, most notably *E. coli*, which for a long time was regarded as the most useful host for gene cloning. However, the inability of *E. coli* to express some biological properties, for example certain metabolic activities, or to carry out appropriate modifications and processing of certain gene products, has encouraged the development of alternative host-vector systems, in particular for different hosts. The use of non-enteric bacteria for basic and applied molecular research has extended the need for well characterised vector systems for such organisms. Thus, vector systems have been designed which are specific for the bacterial species of interest, e.g. soil bacteria. However, a more useful approach would be to design vectors which may be used across a broad range of microbial hosts, and work in recent years has been directed to this.

In addition, expression of foreign genes, and indeed over expression of native genes, can significantly perturb the physiology of the host cell and constitute a strong selective pressure for elimination or inactivation of the cloned genes. Vectors in which the expression of cloned genes can be regulated and controlled have therefore become increasingly important.

The present invention is directed towards meeting this continuing need for new and improved expression vectors for the controlled expression of genes in a wide range of hosts. In particular, it has been found that efficient and controlled expression of cloned genes in a broad range of hosts may be achieved by constructing expression vectors which combine the replicon from the RK2 plasmid family with the expression regulatory functions of the TOL plasmids.

In its broadest aspect, the present invention thus provides an expression vector comprising an RK2 minimum replicon together with an expression cassette comprising the regulatory functions of a TOL plasmid.

As used herein the term "expression cassette" refers to a nucleotide sequence encoding or comprising the various functions required to express a DNA sequence, notably the promoter-operator functions and the associated regulatory sequences required for expression from that promoter, e.g translational and transcriptional control elements and/or sequences encoding regulatory proteins, which may act to regulate expression, for example at the level of the promoter.

RK2 is a well-characterised naturally occurring 60 Kb self-transmissible plasmid of the IncP incompatibility group well known for its ability to replicate in a wide range of gram-negative bacteria (Thomas and Helinski, 1989, in Promiscous Plasmids in Gram-negative bacteria (Thomas, C. M., Ed.) Chapter 1, pp 1–25, Academic Press Inc (London) Ltd, London). It has been determined that the minimal replicating unit of RK2 consists of two genetic elements, the origin of vegetative replication (oriV), and a gene (trfA) encoding an essential initiator protein (TrfA) that binds to short repeated sequences (iterons) in oriV (Schmidhauser and Helinski, 1985, J. Bacteriol. 164, 446–455; Perri et al., 1991, J. Biol. Chem; 266, 12536–12543). This minimal replicating unit is termed the so-called "RK2 minimum replicon", and has been extensively characterised and studied in the literature. A wide range of replicons (termed "mini-RK2 replicons") and cloning vectors based on the RK2 minimum replicon or on derivatives of the RK2 plasmid have been prepared and described in the literature (see, for example, Li et al., 1995, J. Bacteriol. 177, 6866–6873; Morris et al., J. Bacteriol., 177, 6825–6831; Franklin and Spooner, in Promiscous Plasmids in Gram-negative bacteria (Thomas, C. M., ed) Ch. 10, pp 247–267, Academic Press Inc. (London) Ltd., London; Haugan et al., 1992, J. Bacteriol 174:7026–7032; and Valla et al. 1., 1991, Plasmid, 25, 131–136).

The TOL plasmids are another series of well-characterised naturally occurring plasmids and their derivatives, which occur in Pseudomonas sp. and which encode the enzymes required for the catabolism of toluene and xylenes (for a review see Assinder and Williams 1990, Adv. Microb. Physiol., 31, 1–69).

The catabolic genes of TOL plasmids are organised in two operons, an upper pathway operon (OP1) encoding genes and regulatory sequences required for the oxidation of aromatic hydrocarbons to aromatic carboxylic acids, and a lower, or meta pathway operon (OP2) necessary for the oxidation and ring clearage of the aromatic nucleus of aromatic carboxylic acids, giving rise to intermediates which are channelled into the intermediary metabolism. The expression of the two operons is controlled by two positive regulatory proteins XylR and XylS, in the presence of the corresponding substrate ligands toluene/xylene and benzoate/toluate respectively. Activated XylR stimulates transcription from the Promoter Pu of the upper pathway operon, whereas activated XylS induces the meta pathway operon from the promoter Pm. XylR may also induce the promoter Ps of the xylS gene (see Assinder and Williams, Supra). A regulatory cassette based on the xylR gene and Pu promoter has been described and used to prepare expression vectors which enable regulated gene expression induced by aromatic hydrocarbons (Keil and Keil, 1992, Plasmid, 27, 191–199). However, it has not previously been proposed to combine the TOL regulatory functions Pu/xylR or Pm/xylS with an RK2-based replicon within an expression vector construct.

Viewed from a further aspect, the present invention thus provides an expression vector comprising a RK2 minimum replicon together with a promoter Pm and/or Pu and a corresponding regulatory gene xylS and/or xylR as derived from a TOL plasmid.

In such expression vectors of the invention the catabolic genes of the TOL plasmids, encoding the enzymes of the metabolic pathway, are generally absent. Especially, the full complement of catabolic structural genes, in any one, or both, of the operons, are absent.

The novel vectors of the invention allow the regulated expression of cloned genes in a wide range of host cells.

As mentioned above, the RK2 replicon has been well studied and its complete nucleotide sequence is reported (Pansegrau et al., 1994, J. Mol. Biol., 239, 623–633). Thus, sources for the RK2 minimum replicon are well established and readily available. Hence, for example, the RK2 minimum replicon may be derived from the parental plasmid RK2 or from any of the vast number of derivatives or mini RK2 plasmids described and available from the literature (see e.g. Li et al; Morris et al., Franklin and Spooner; Haugen et al; and Valla et al., Supra). As exemplary of a suitable source plasmid for the minimum RK2 replicon may be mentioned plasmid pFF1 (Durland et al., 1990, J. Bacteriol, 172, 3859–3867), but many other source plasmids are available and could be used. The separate elements of the minimum replicon, oriV and the trfA gene may be isolated from the same source together or separately or from separate sources.

Likewise, any of the TOL plasmids and their derivatives widely known and described in the literature could be used as the source of the TOL regulatory functions (see e.g. Assinder and Williams, Keil and Keil, Supra and Mermod at al., 1986, J. Bacteriol., 167, 447–454). Indeed, a number of plasmids are known in the literature which have TOL genes inserted, and any of these could be used as the source of the TOL regulatory functions for the present invention. The regulatory genes xylR and/or xylS may be inserted together with the Pu and/or Pm promoter from the same source or the promoter and regulatory gene may be derived independently from separate sources. Thus, for example a Pm promoter may be derived from plasmid pERD21, (a RSF1010-based replicon, Ramos at al., 1988, Febs Letters, 226, 241–246), a Pu promoter may be derived from plasmid pRD579 (an R1-based replicon, Dixon at al., 1986, Molec. Gen. Genet. 203, 129–136), a xylS gene may be derived from plasmid pERD839 (a plasmid based on the RSF1010 replicon, Michan et al., 1992, 267, 22897–22901; this publication also mentions other plasmids which may be the source of xylS genes, e.g. pERD103 for wild-type xylS) and a xylR gene may be derived from plasmid pTS179 (a pACYC184 replicon, Inouye et al., 1983, J. Bacteriol., 155, 1192–1199. Alternatively the Pu/xylR expression cassette of Keil and Keil (supra) could be used. These sources are however only exemplary, and a number of alternative source plasmids could be used, selected from among the vast number known in the literature.

Techniques for excising the desired nucleotide sequences containing the TOL promotor and/or regulatory regions or the RK2 minimum replicon functions from a selected source and introducing them into an expression vector or intermediate construct are well known and standard in the art, and are described for example in Sambrook at al., 1989, Molecular cloning; a laboratory manual, 2nd Edition, Cold Spring Harbour Laboratory Press, Cold Spring Harbour, N. Y.

As will be described in more detail in the Examples below, it is convenient to isolate the desired sequences from a selected source and introduce them, using techniques standard in the art, into a series of intermediate constructs, which may be plasmids, introducing or adding or deleting elements to arrive at the expression vectors of the invention.

As used herein the terms "RK2 minimum replicon" and "TOL regulatory functions" and indeed the separate genetic elements "oriV", "trfA" "Pm", "Pu", "xylS" and "xylR" include not only the native or wild-type functions as they appear in the original, parental or archetypal source plasmids but also any modifications of the functions, for example by nucleotide addition, deletion, or substitution or indeed chemical modification of the nucleotides, which occur naturally, e.g. by allelic variation or spontaneous mutagenesis, or which are introduced synthetically. Techniques for modification of nucleotide sequences are standard and well known in the literature and include for example mutagenesis, e.g. the use of mutagenic agents or site-directed mutagenesis. PCR may also be used to introduce mutations. Appropriate or desired mutations, may for example be selected by mutant screening of the genetic element in question e.g. the promoter.

Thus, modifications may be introduced into the trfA gene, for example, to increase copy number of the vector within a host cell, or to achieve temperature sensitive replication. Such modifications have been described in the literature. The copy number of RK2 within E. coli is usually estimated to be 5–7 plasmids per chromosome. However, this may be elevated in both E. coli and other bacteria by certain point mutation in the trfA gene, which may lead to copy numbers up to 23-fold higher than normal. Such "copy up" or "cop mutations" are described for example in Durland et al., 1990, J. Bacteriol, 172, 3859–3867; Haugan et al., 1992 supra; and Haugan et al., 1995, Plasmid, 33, 27–39. Cop mutations have been shown to be most effective in increasing copy numbers in E. coli; in other bacteria, such high copy numbers may not be tolerated. Nonetheless, cop mutations in the trfA gene may be used to increase expression in bacterial species beyond E. coli.

Results have shown that expression of genes from the vectors of the invention may be modified by changing the copy number of the vectors. This is a unique and useful feature, which could be used, for example, to reduce expression due to the formation of inclusion bodies. A lower copy number of cop plasmids may also be used to reduce background and gene expression, in the absence of inducer. This may be particularly useful if the gene product is toxic to the host cell.

Studies have shown that cop mutations in trfA tend to be localised between the Nde I and Sfi I sites in trfA, and that cop mutations may readily be prepared by exchanging the Sfi I/Nde I fragment internally in the trfA gene, and straight-forward one-step cloning procedures (see Haugan et al., 1995, supra). It is therefore advantageous to keep the Sfi I and Nde I sites in trfA unique in the vectors of the invention. Mutations may also be introduced into trfA to render the replication of RK2-oriV plasmids temperature sensitive, as described for example in Valla et al., 1991 and Haugan et al., 1992, supra. The trfA gene is known to encode two related proteins of 44 and 33 kDa that are produced by independent translation initiation at two start codons within the same open reading frame (Shingler and Thomas, 1984, J. Mol. Biol. 175, 229–249). Mutations may be introduced using analogous techniques to alter other functional properties of these proteins.

Within the scope of the invention, vectors may be created which permit regulated expression of trfA, permitting replication of the vector to be controlled. Thus, for example, vectors have been constructed in which trfA is placed under control of the Pm promoter. This may be achieved simply by deleting trfA from its original position in a vector of the invention such as pJB653ATG (see Example 1) and inserting it downstream of Pm. Vectors in which trfA is under the control of Pu may analogously be constructed. The useful property of such vectors is that they replicate as long as the promoter is kept induced by the presence of the external inducer (i.e. an aromatic hydrocarbon), while replication is blocked in the absence of the inducer; a certain minimum amount of TrfA protein is required for replication and if insufficient TrfA is expressed the vectors cannot replicate, which generally occurs in the absence of inducer (although this is dependent on cell growth temperature—see Table 8).

Vectors which allow controlled trfA expression may have a number of uses. For example, if a cop mutant of trfA is used, the copy number of the plasmid may be controlled by the inducer, indirectly making it possible to control the expression level of a gene controlled by another promoter. The vectors could also be used to insert transposons and inactivate specific genes by homologous recombination. Thus, the vector may be established in a host, the culture grown in the presence of inducer, and then plated onto selective plates in the absence of inducer. Only those cells where transposition or recombination has taken place will survive.

The ability to control trfA expression may be of interest from a safety point of view. The expression system makes it possible to eliminate the vector after production, since its existence is dependent on the particular inducer.

Modifications may also be introduced to any of the TOL-based regulatory functions. Thus, modifications, e.g. by introduction of point mutations including either by random or site-directed mutagenesis, may be made to the promoters Pu or Pm or to the regulatory genes xylR or xylS, for example to improve expression, alter the regulatory characteristics, or to extend the host range of the vectors, etc. For example, a mutant of the Pm promoter which exhibits down-regulation of expression, which might be useful in some circumstances, is reported in Kessler et al., 1993, J. Mol. Biol. 230, 699–703. Conversely, mutations to enhance expression may also be made. Thus, for example, expression could be increased by expressing more XylS, as described for example by Kessler a al., 1994, J. Bacteriol., 176, 3171–3176. A number of modifications of the xylS gene have also been reported, for example the xylS mutant xylS2tr6, which exhibits an altered effector specificity, and can mediate a 3–8 fold higher level of transcription than can wild-type xylS at a wide range of temperatures (Ramos et al., supra), and the mutant gene xylSarg41pro (=xylS839), which causes a reduction in the basal transcription level from Pm, compared to wild type xylS (Michan et al., supra). All such modifications may be used according to the present invention.

It has also been found that the xylR/xylS genes may be inserted into the vectors in either orientation.

As mentioned above, the expression vectors of the invention may advantageously be used to express a desired gene within a broad range of host cells. It has surprisingly been found that high level and tightly controlled expression may be obtained across a broad range of hosts using the same vector system. This high level of expression maintained across a range of hosts is an unusual feature. In addition to the broad host range of the vectors, the Pu and Pm promoters give a very high induced to uninduced ratio, indicating that tight control of expression may be achieved. Especially, it has been observed that levels of expression from the Pm promoter are surprisingly high for different genes and for different hosts, as compared with Pu or other promoters. The use of a Pm promoter therefore represents a preferred aspect of the invention.

Transcription from the Pu and Pm promoters can be activated by different inducers, and different inducer compounds can lead to different levels of promoter activation (Ramos et al., 1990, J. Mol. Biol. 211, 373– 382). This property may also be used to fine-tune expression levels.

It may also be possible, further to modify expression levels by modifying culture conditions. Thus, the expression system may be improved by changing the growth condition of the host cell, e.g. temperature, culture medium composition and other culture conditions such as speed of agitation, vessel size etc. Such culture modifications are known in the art. It has been found, for example, that expression increases at lower temperature. It may further be possible also to modify expression from Pu by means of catabolite repression, for example by adding certain sugars, e.g. glucose to the growth medium during culture of the host cells.

The "genes" which may be expressed in the vectors of the invention include any desired or cloned genes including partial gene sequences, or any nucleotide sequence encoding a desired expression product, including fusion protein products, such as, for example, a desired gene sequence linked to a further nucleotide sequence encoding a further polypeptide such as β-galactosidase or glutathione-S-transferase. Such "fusion proteins" are well known in the art. The genes which are expressed from the vectors of the invention may thus include genes which are heterologous or homologous to the host cell.

The host range of the vectors is broad and includes a vast range of Gram-negative bacteria, as well as Gram-positive bacteria. Suitable Gram-negative bacteria include all enteric species, including, for example, Escherichia sp., Salmonella, Klebsiella, Proteus and Yersinia. and non-enteric bacteria including Azotobacter sp., Pseudomonas sp., Xanthomonas sp., Caulobacter sp, Acinetobacter sp., Aeromonas sp., Agrobacterium sp., Alcaligenes sp., Bordatella sp., Haemophilus Influenzae, *Methylophilus methylotrophus*, Rhizobium sp. and Thiobacillus sp. (see also Thomas and Helinski, supra). Gram-positive bacterial hosts which may be used include Clavibacter sp.

Such transformed host cells are included within the scope of the present invention. A further aspect of the present invention thus includes a host cell containing an expression vector as hereinbefore defined.

Methods for introducing expression vectors into host cells and in particular methods of transformation of bacteria are well known in the art and widely described in the literature, including for example in Sambrook et al., (supra). Electroporation techniques are also well known and widely described.

In a still further aspect, the invention thus also provides a method of expressing a desired gene within a host cell, comprising introducing into said cell an expression vector as hereinbefore defined containing said desired gene, and culturing said cell under conditions in which said desired gene is expressed.

Advantageously, the desired gene may encode a desired polypeptide product and hence the invention also provides a method of preparing such a desired polypeptide product by culturing a host cell containing an expression vector of the invention into which the desired gene has been introduced, under conditions whereby said polypeptide is expressed, and recovering said polypeptide thus produced.

To express the desired genes, the expression vectors of the invention conveniently contain one or more sites for insertion of a cloned gene, e.g. one or more restriction sites, located downstream of the promoter region. Preferably, multiple, e.g. at least 2 or 3, up to 20 or more, such insertion sites are contained. Vectors containing multiple restriction sites have been constructed, containing eg. 20 unique sites in a polylinker. Suitable cloning sites for insertion of a desired gene are well known in the art and widely described in the literature, as are techniques for their construction and/or introduction into the vectors of the invention (see eg. Sambrook et al., supra).

For ease of construction, appropriate cloning sites may be introduced in the form of a polylinker sequence, using nucleic acid manipulation techniques which are standard in the art. A range of suitable polylinker sequences are known in the art and may simplify the routine use of the expression vectors. Thus, for example a well-known polylinker/lacZ' region may be used, as described for example in the vectors of Ditta et al., 1985, Plasmid, 13, 149–153, simplifying standard cloning procedures and identification of plasmids with inserts, by using the blue/white selection technique based on lacZ, which is well-known in selection procedures.

A number of other features may also be included in the vectors of the invention. Thus, the vectors may include features which assist in plasmid transfer, such as the oriT function of RK2 plasmids, which facilitates conjugation and is useful in cases where transformation/electroporation is inefficient, or if very high transfer frequencies are required.

Functions may also be introduced to stabilise the expression vectors, or to assist in their maintenance in a broad range of hosts. RK2 encodes two operons containing the parDE and parcBA genes, respectively, which are involved in the maintenance of RK2 plasmids or heterologous replicons in diverse bacterial hosts (Roberts et al., 1990, J. Bacteriol, 172, 6204–6216; Schmidhauser and Helinski, supra; Sia et al., 1995, J. Bacteriol, 117, 2789–2797; and Roberts et al., 1992, J. Bacteriol, 174, 8119–8132). Par functions or loci, including any of the par genes eg parDE may thus be introduced into the vectors of the invention.

Selectable markers are also usefully included in the vectors of the invention for example to facilitate the selection of transformants. A wide range of selectable markers are known in the art and described in the literature. Any of these may be used according to the present invention and include for example the antibiotic resistance markers carried by the RK2 plasmids and their derivatives, or indeed any of the TOL plasmids or their derivatives, or any other plasmid. However, properties such as sugar utilisation, proteinase production or bacteriocin production or resistance may also be used as markers. The TOL plasmid xylE structural gene may also be used as a marker. This gene encodes the product C230 which may readily be detected qualitatively or assayed. Spraying a plate of bacterial colonies with catechol rapidly distinguishes C230$^+$ colonies since they turn yellow due to the accumulation of 2-hydroxy muconic semialdehyde, enabling transformants/transconjugants etc. rapidly to be identified, by the presence of xylE in the vectors.

Other features which may be included in the vectors include further regulatory and/or enhancer functions, for example transcriptional or translational control sequences such as start or stop codons, transcriptional initiators or terminators, ribosomal binding sites etc. Thus, for example, in vectors where trfA expression is not controlled, a transcriptional terminator, preferably a bidirectional terminator, may advantageously be positioned between the promoter and the trfA gene. In this way read-through transcription from the trfA gene into the Pu/Pm promoters may be prevented and transcription initiated at Pu or Pm should not affect trfA expression. It will however be appreciated that the use of transcriptional terminators has general applicability to avoid read-trough transcription of protein encoding portions of the vector, such as the trfA gene and the cloned gene of interest. Such functional elements are known in the art and a suitable transcriptional terminator is described in, for example, Fellay et al., 1987, Gene, 52, 147–154 and Frey and Krisch, 1985, Gene, 36, 143–150. As will be described in more detail in the Examples below, whilst TOL-based control elements such as start codons or ribosomal binding sites etc. naturally associated with the Pu/Pm promoters may be used, alternative or additional such elements may also be introduced. Example 1 describes the preparation of an ATG expression vector, where sequences downstream of the ATG initiator were eliminated, permitting gene sequences to be inserted directly in this ATG site. A vector construct has also been created in which bases between the promoter and Shine-Dalgarno sequence are modified to create a new restriction site. Thus, the vector pJB653ATG of Example 1 has been modified in this fashion, making it possible to combine mutations in the Shine-Dalgarno sequence with mutations in the promoter.

Further modifications which may be made to the vectors, include size reduction by removal of unnecessary DNA from source or intermediate plasmids, removal of undesired restriction sites, addition of new restriction sites etc., which may be achieved by standard DNA manipulation techniques.

As mentioned above, the high levels of expression obtainable across a broad host range, make the expression vectors of the present invention particularly useful as tools for maximising and/or controlled expression of a desired gene product. Control of trfA expression permits a further means of regulating or controlling expression of a desired gene product. The vectors may also be used for expression studies and physiological analyses in bacteria, for example to analyse metabolic pathways, eg. determine rate limiting steps, conveniently also at intermediate or low expression levels, or for studies of plasmid transfer and dispersal in natural environments. The vectors of the invention may have particular utility as an environmental safety standard. The vectors of the invention, since they allow expression, and indeed in some cases replication of the vector, to be tightly controlled, are particularly safe from an environmental point of view. In particular, the trfA controlled vectors would not be able to replicate in the natural environment, due to the absence of the inducer (except under certain cell growth temperatures—see Table 8), were they to escape into the environment, as a result of, for example, leakage of host cells from a fermentor. Thus, the vectors present in the escaped cells would eventually be eliminated as the escaped cells propagated, since the vectors would be unable to replicate, thereby also eliminating the inserted foreign gene from the environment.

Figure 1B:
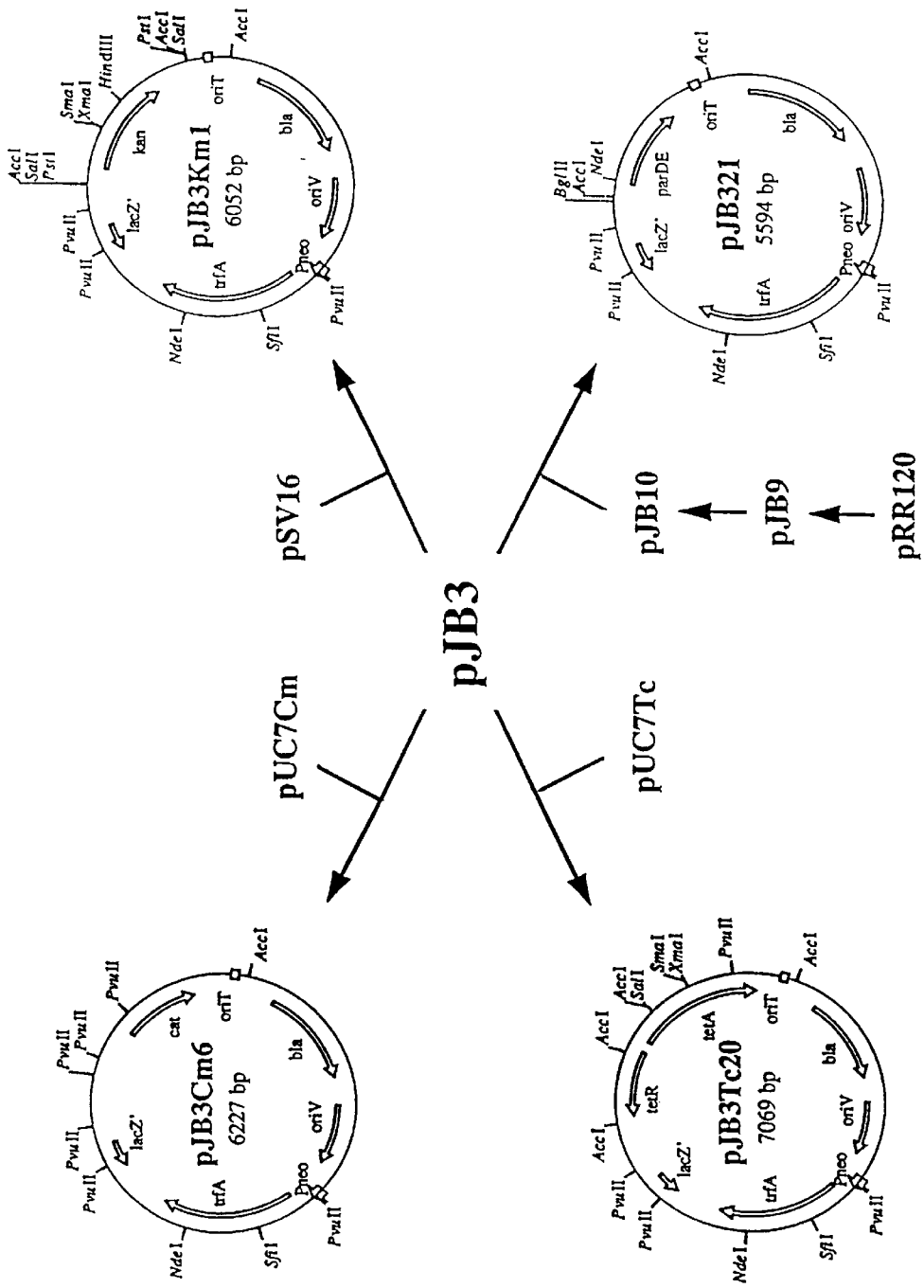

The invention will now be described in more detail in the following Examples, with reference to the following drawings in which:

FIG. 1 shows a map and the construction of general purpose broad host-range cloning vectors. Restriction sites relevant for the construction or use of the vectors are shown. Each step in the construction is indicated by an arrow. The restriction sites in the polylinker downstream the lacZ promoter is marked with ▼, and the sites are, in the counterclockwise direction; HindIII, SphI, PstI, SalI/HincII/ AccI, XbaI, BamHI, XmaI/SmaI, KpnI, SacI, and EcoRI. Sites in the polylinker that are not unique are indicated elsewhere on each vector. Note that the sites for NdeI and SfiI are unique for all the vectors, except for pJB321.

Figure 2A:
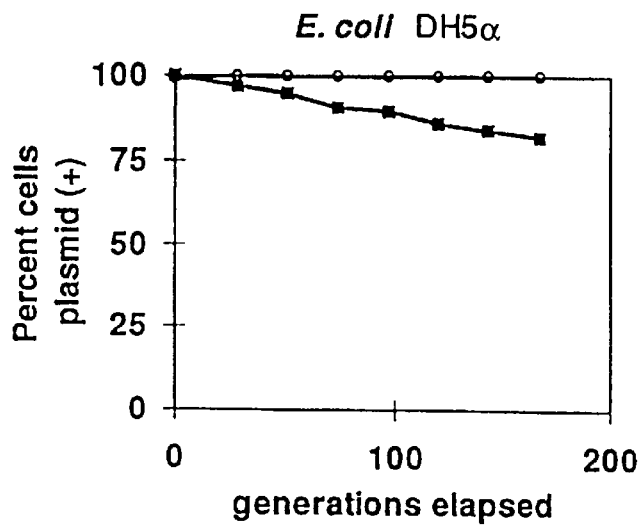
Figure 2B:
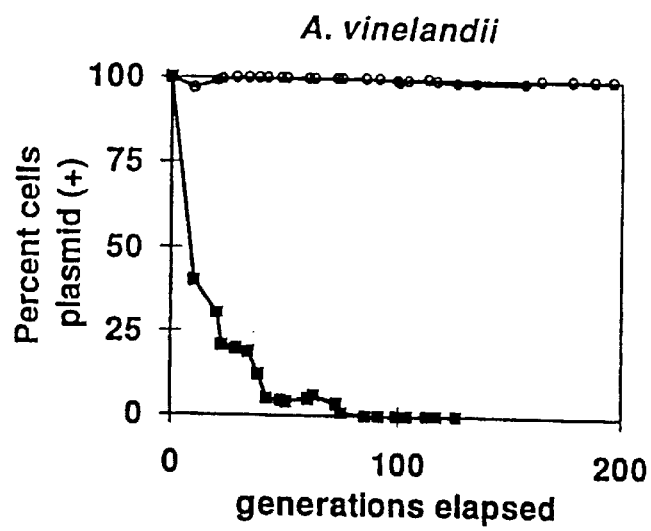
Figure 2C:
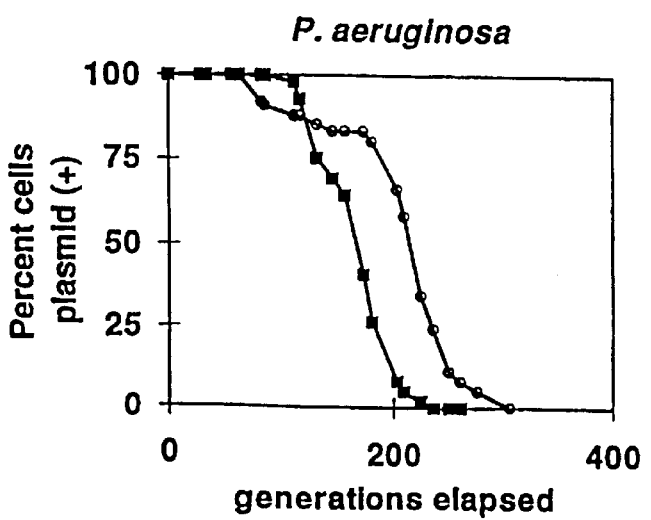

FIGS. 2A–2C presents graphs showing the broad host-range stabilization properties of the 0.8 kb parDE region in vector pJB321E. In various species: (A) *E. coli* DH5α; (B) *A. vinelandii*; (C) *P. aeruginosa*. Symbols: ■, pJB3E; °, pJB321E.

Figure 3A:
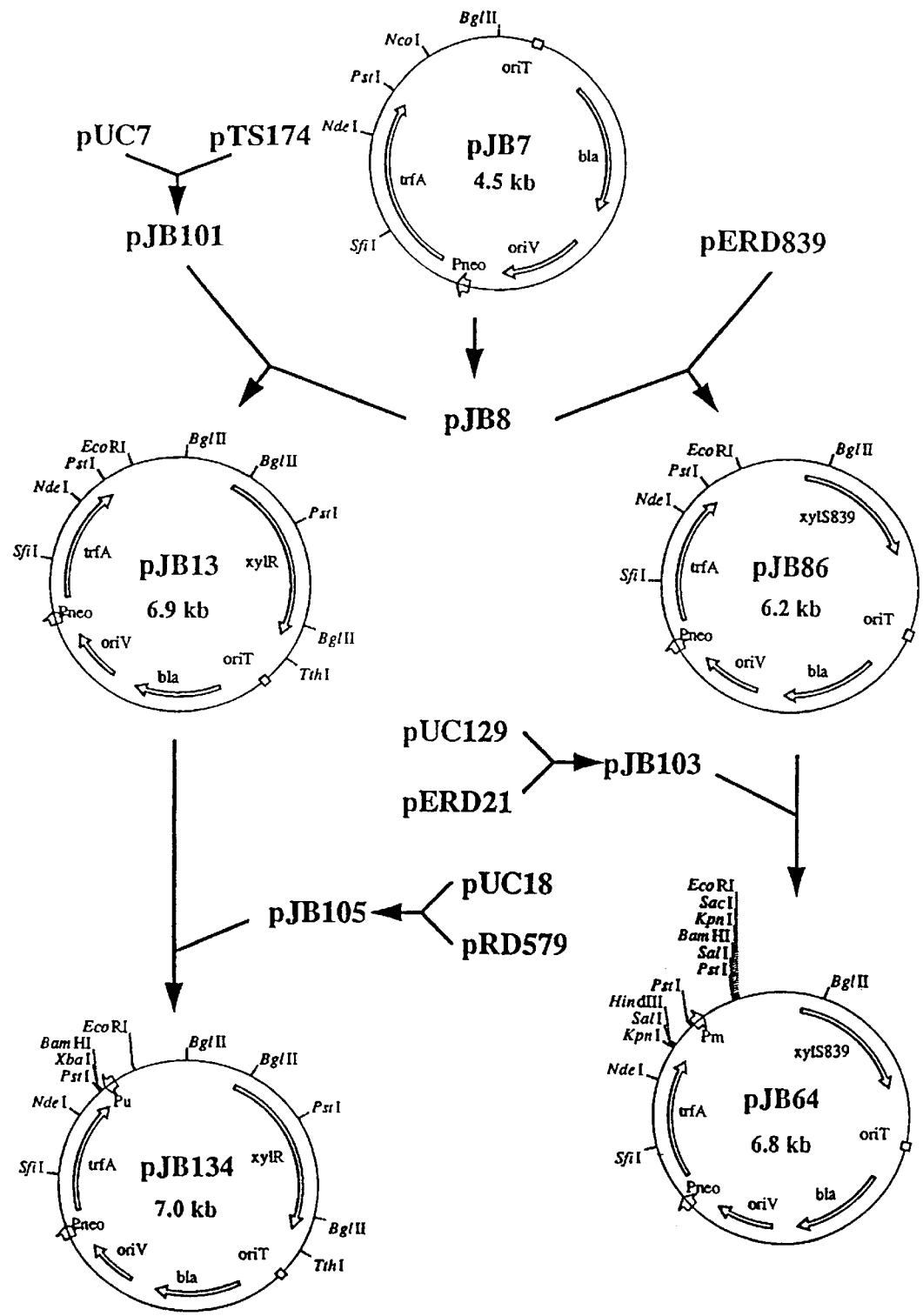
Figure 3B:
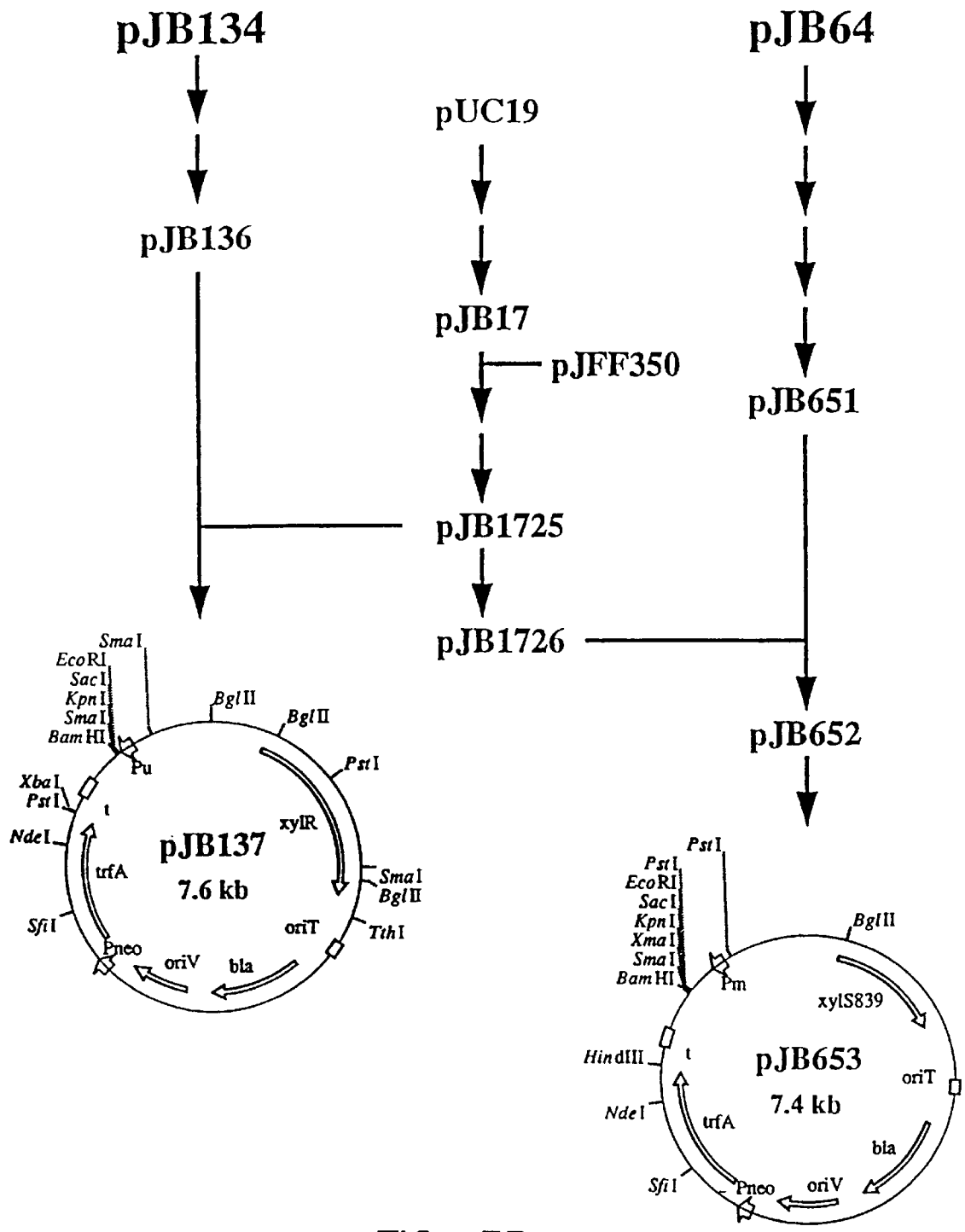

FIG. 3 shows a map and the construction of broad host-range expression vectors pJB137 and pJB653. The sites in the polylinker (originally from pUC19) downstream of the promoters Pm and Pu are indicated. Other notations are as described in the legend to FIG. 1. NdeI and SfiI are unique in all the vectors, except for in the parDE derivatives pJB139 and pJB654 (Table 1).

Figure 4A:
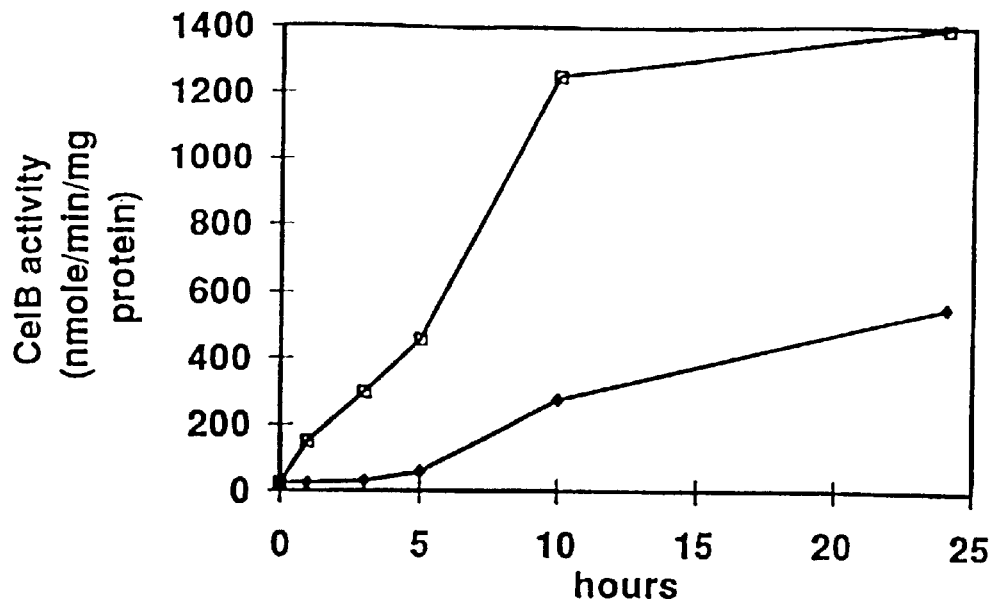
Figure 4B:
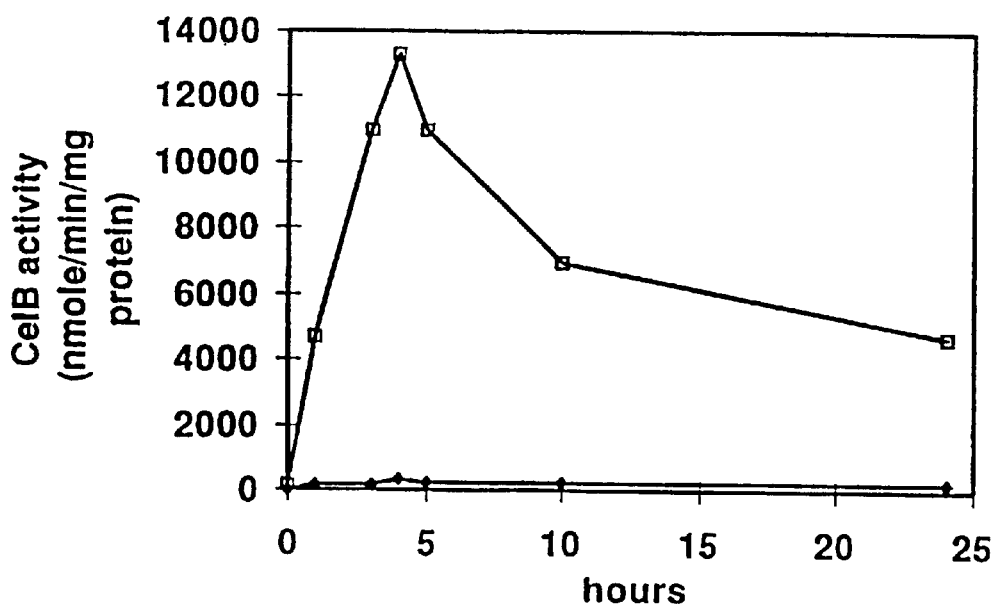

FIGS. 4A–4B presents graphs showing Expression analysis of celB as a function of cell growth in *E. coli* PGM1. (A). Expression from pJB137celB (Pu). (B) Expression from pJB653celB (Pm). The basal expression level of celB from Pm is between 200 and 300 nmole/min/mg protein. (□) presence; (♦), absence of inducer dated at t=0.

Figure 5:
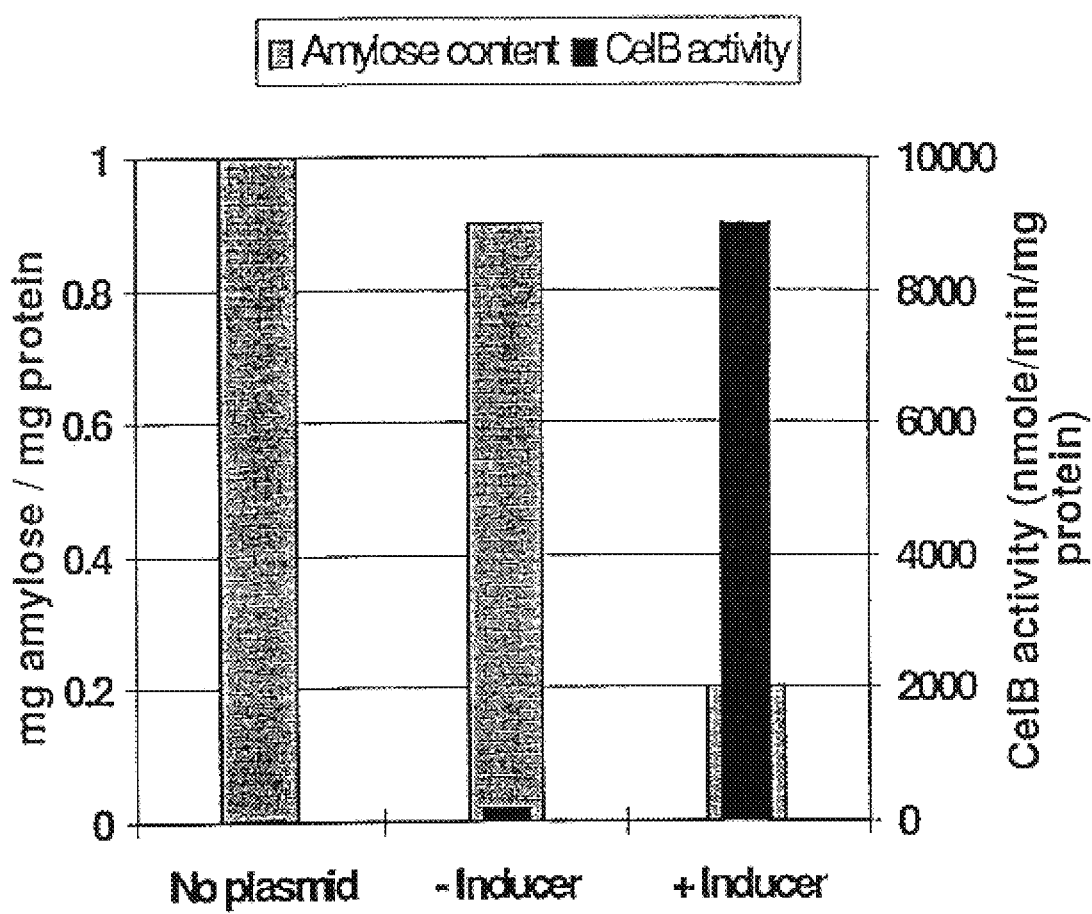

FIG. 5 shows amylose combination in *E. coli* PGM1 as a function of celB expression from pJB653celB.

Figure 6:
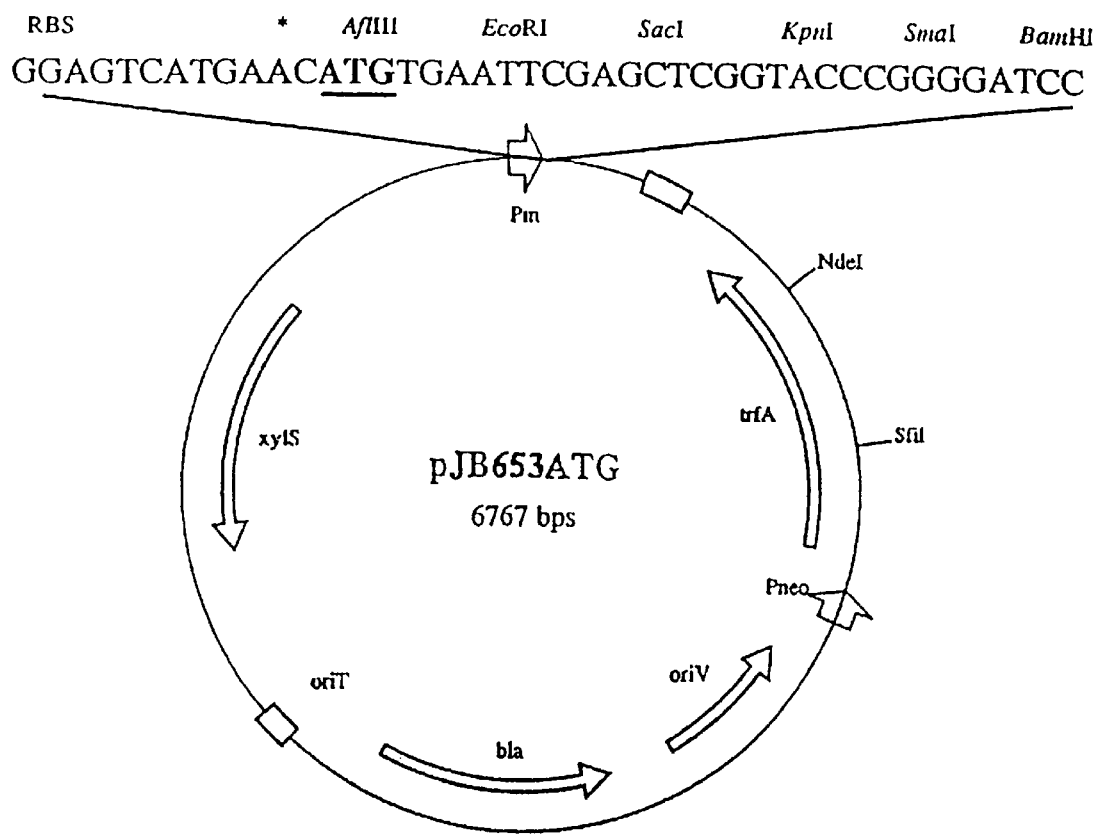

FIG. 6 shows a map of pJB653ATG. pJB653ATG differs from pJB653 by lacking 275 bp downstream of the translation initiation ATG (underlined in SEQ ID NO: 1) and by the construction of an AflIII site at the initiating ATG by changing one base from C to A (marked with the symbol *). Note that pJB653ATG contains a unique PstI site, in contrast to pJB653, which contains two such sites (FIG. 3); RBS; ribosome binding site (32).

Figure 7A:
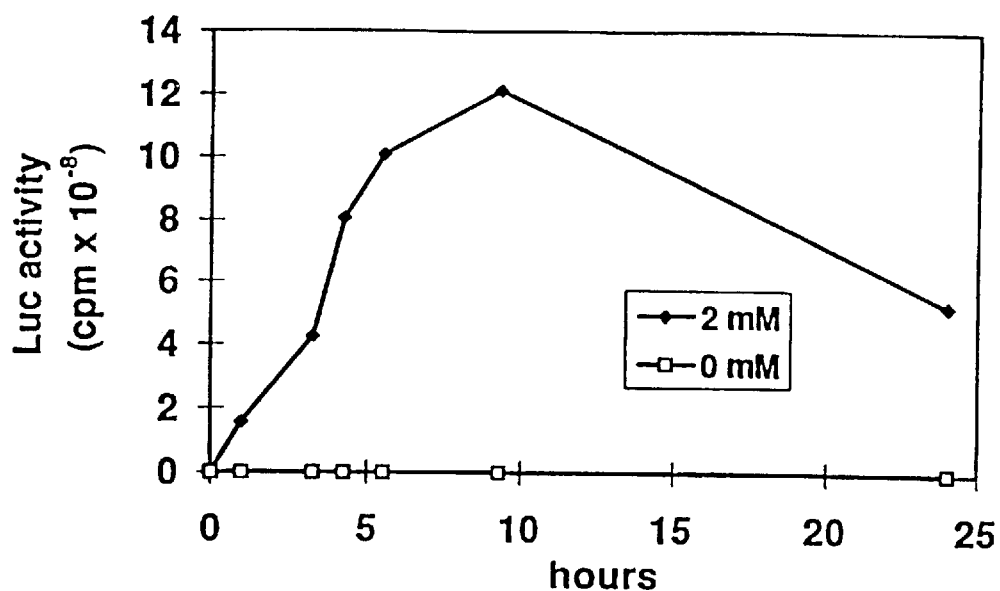
Figure 7B:
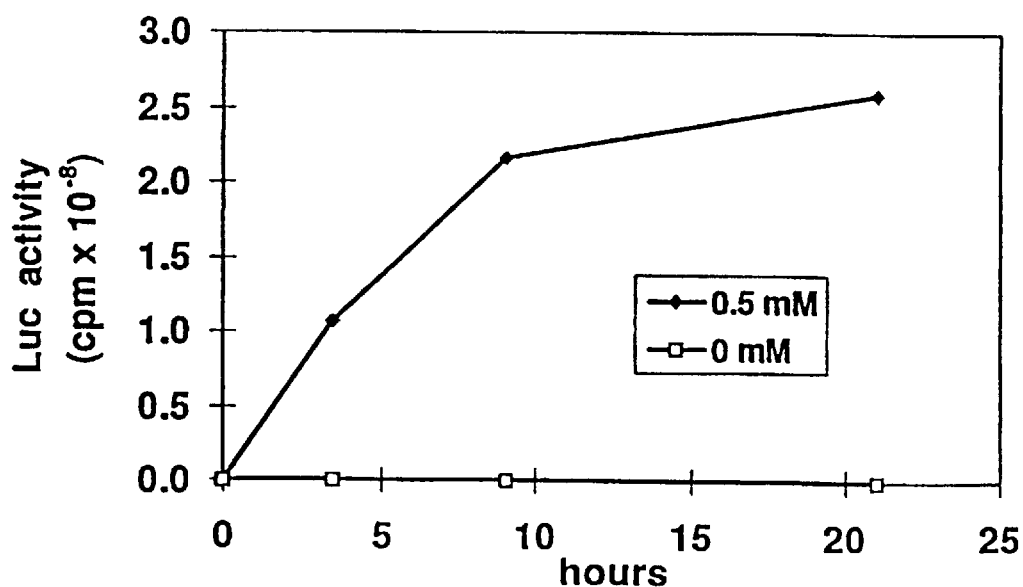
Figure 7C:
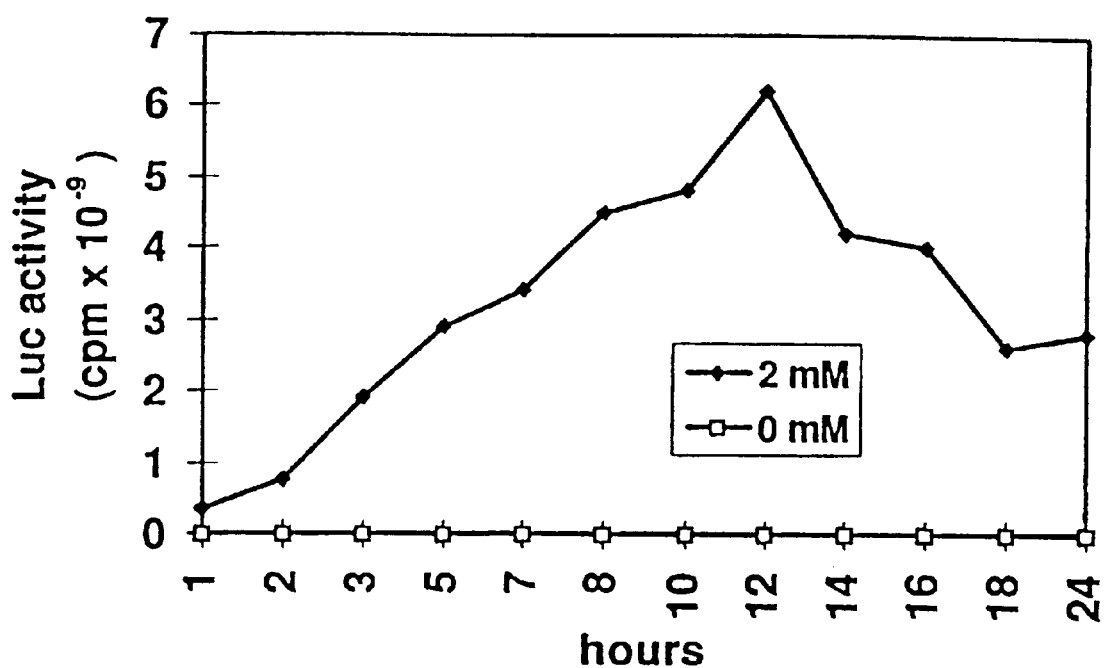

FIGS. 7A–7C presents graphs showing the expression of luc from pJB653ATGluc in (A) *E. coli* DH5α, (B) *X. campestris* and (C) *P. aeruginosa* as a function of cell growth in the presence (♦) and absence (□) of inducer. The basal expression levels of Luc from Pm in *E. coli*, *X. campestris* and *P. aeruginosa* are $4 \times 10^6$, $8 \times 10^5$ and $5.1 \times 10^7$ cpm, respectively (average values). [a] The cpm values correspond to the activity in 10 µl cell culture at $OD_{660}=0.3$.

Figure 8:
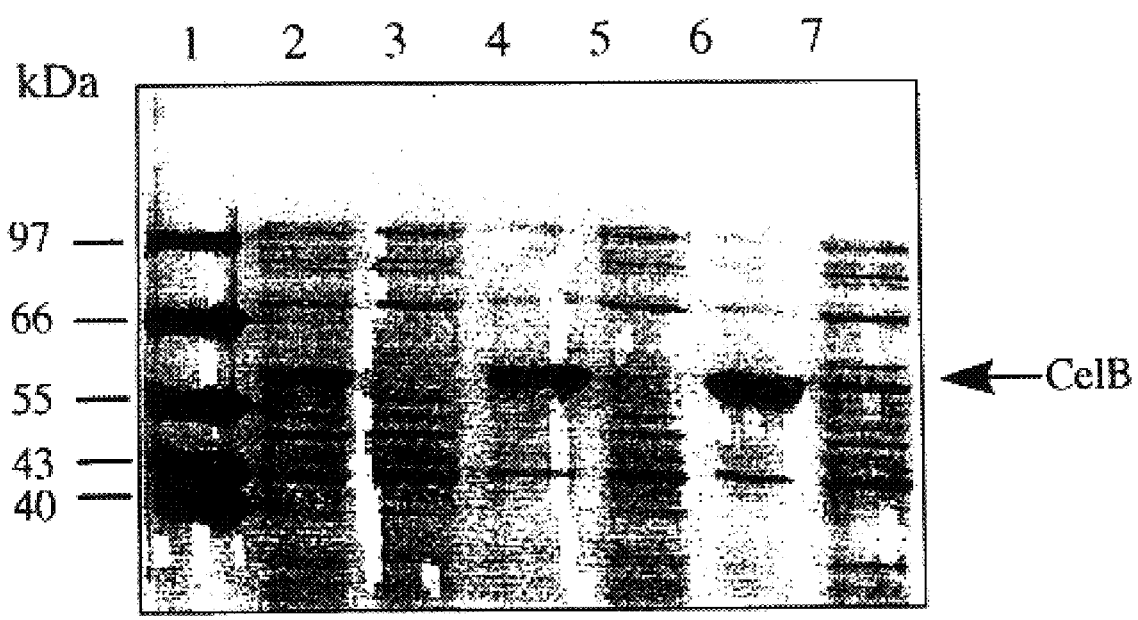
Figure 9:
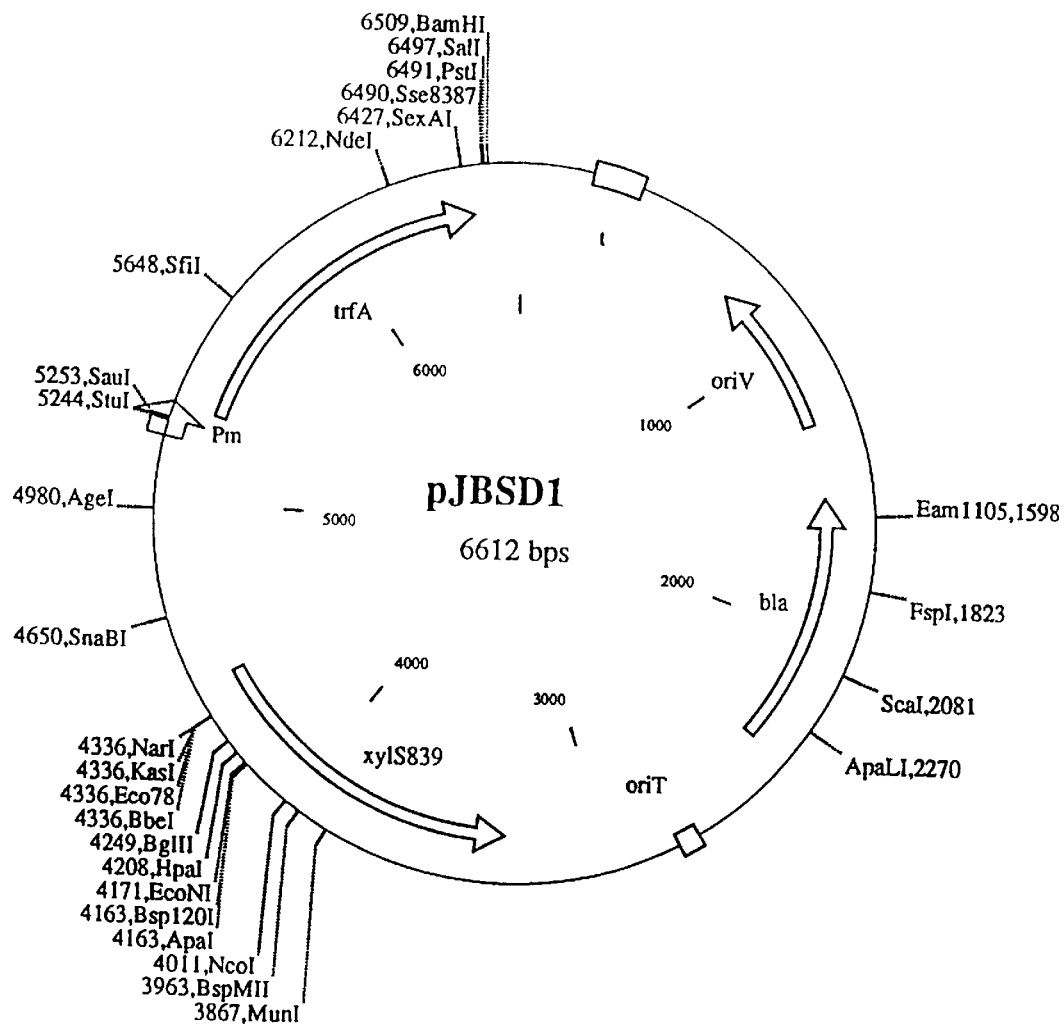

FIG. 8 shows an SDS-PAGE gel of samples of protein expressed in *E. coli* DH5α from the "CelB" vectors of Example 2; lane 1: Molecular weight standard. lane 2: DH5α (pJB653ATGceiB) induced. lane 3: DH5α (pJB653ATGcelB) uninduced. lane 4: DH5α (pJB653ATGcelBcop271C) induced. lane 5: DH5α (pJB653ATGceiBcop271C) uninduced. lane 6: DH5α (pJB653ATGcelBcop251M) induced. lane 7: DH5α (pJB653ATGcelBcop251M) uninduced;

FIG. 9 shows a map of vector pJBSD1, as described in Example 4.

EXAMPLE 1

In this Example we describe the construction of a series of well characterized broad host-range multi-purpose cloning vectors based on the RK2 replicon. These vectors were used to develop tightly controlled gene expression systems. For this purpose we used the Pu/Pm promoters and the corresponding positive regulatory genes xylR/xylS, all originating from the TOL plasmid of *Pseudomonas putida*.

To characterise the functionality of the two promoters, we used the genes encoding the enzymes phosphoglucomutase (CelB) from *Acetobacter xylinum* (Fjærvik, et al., 1991, FEMS Microbial. Lett., 77, 325–330), and luciferase from the firefly *Photinus pyralis*. Amylose accumulation in *E. coli* was used as a model to study the intracellular effects of varying CelB expression, since *E. coli* cells lacking phosphoglucomutase (in contrast to wild type) accumulate amylose intracellularly when grown on maltose as carbon source (Adhya Pt al., 1971, J. Bacteriol., 108, 621–626).

The use of luciferase as a reporter was motivated by the fact that microorganisms generally do not naturally express this enzyme, in contrast to phosphoglucomutase.

Materials and Methods
Bacterial Strains, Plasmids and Growth Media.

The bacterial strains and plasmids used in this study are described in Table 1. *P. aeruginosa* and *E. coli* strains were grown in L-broth or on L-agar (Sambrook et al., supra). In the amylose accumulation experiments L-broth was supplemented with 1% maltose. The growth temperature was 30° C. for *P. aeruginosa*. *E. coli* cells were grown at 37° C., except for the expression analysis of celB and luc transcribed from the Pm/Pu promoters, where 30° C. was used. *A. vinelandii* and *X. campestris* were grown at 30° C. in Burk medium (Schmidhauser and Helinski, supra) and YM broth (Difco), respectively. Antibiotics were used at the following concentrations: ampicillin, 100 µg/ml (wild type trfA), 1 mg/ml (cop271C), or 2 mg/ml (cop254D); carbenicillin, 100 µg/ml; tetracycline, 15 µg/ml; chloramphenicol, 30 µg/ml; kanamycin, 50 µg/ml; streptomycin, 2 mg/ml.

Conjugative Matings and Electrotransformations.

Conjugative matings from *E. coli* to *P. aeruginosa* were performed on membranes and the mixtures were incubated on nonselective agar-medium at 30° C. for 3 hours. S17.1 containing the relevant plasmids was used as donor strain. The mating mixture was incubated for 3 hours at 30° C. and then plated on agar-medium containing carbenicillin and streptomycin. Plasmids were transferred to *A. vinelandii* and *X. campestris* by electrotransformation at a field strength of 12.5 kV/cm, as described for *E. coli* (Hanahan et al., 1991, Methods Enzymol, 204, 63–113) and the cells were then plated on agar-medium containing ampicillin.

DNA Manipulations.

Plasmid DNA was prepared by the alkaline lysis protocol for *E. coli*, and all other standard techniques were performed according to Sambrook et al, supra. Transformations of *E. coli* were performed by the method of Chung et al., 1989, Proc. Natl. Acad. Sci., USA, 86, 2171–2175. DNA sequencing was performed by the dideoxy chain-termination method (Sanger et al., 1977, Proc. Natl. Acad. Sci., 74, 5463–5467). Cell growth at $OD_{660}$ was monitored with a Beckman DU-65 (celB expression experiments) and a Shimadzu UV-160A spectrophotometer (luc expression experiments). For PCR amplification of the luc gene from pGEMluc the following primers were synthesized; 5'GATCCCCATG-GAAGACGCCAA3' (SEQ ID NO: 2) and 5'CGGAG-GATCCCAATAGCTAAGAA3' (SEQ ID NO: 3). The primers contain a NcoI and a BamHI site, respectively. For PCR amplification of the 139 bp EcoRI/PstI fragment, using pJB653 as template, the following primers were used; 5'AGGTGAATTCACATGTTCATGACTCCA3' (SEQ ID NO: 4) (containing an EcoRI and an AflIII site), and 5'AGGGCTGCAGTGTCCGGTTTGA3' (SEQ ID NO: 5) (containing a PstI site).

Analysis of Plasmid Stability.

*E. coli* DH5α, *A. vinelandii* and *P. aeruginosa* containing pJB3E/pJB321E were grown under selection to stationary phase, diluted 100-fold in the same medium and then grown exponentially under selection. The stability assay was initiated by diluting the cells to $1 \times 10^3$ cells/ml in non-selective medium, followed by growth over night. Cultures were then again diluted and grown overnight in non-selective medium (as above), and this procedure was repeated until the total number of generations had reached 200–400, as indicated in the Results Section. After each dilution aliquots were plated on nonselective agar medium. The colonies were sprayed with 50 mM catechol to monitor the frequency of plasmid-containing cells (yellow colonies, Franklin at al., 1981, Proc. Natl. Acad. Sci, 78, 7458–7462).

The results were also double-checked by replica plating 100 colonies on agar-medium containing ampiciilin.

Expression Studies and Amylose Measurements.

For CelB and Luc expression studies referring to FIG. 4, FIG. 7, and Table 3, cells were grown overnight in selective medium, diluted 100-fold in the same medium and then grown exponentially to $OD_{660}=0.1$. Stimulation of celB and luc transcription from the Pm promoter was then induced by addition of m-toluic acid to 2 mM or 0.5 mM for *E. coli* and *X. campestris*, respectively. 0.5 mM IPTG was used for inducing luc expression from the ptrc promoter in pTrc99Aluc. Cells containing pJB137celB were diluted again (2000-fold) and grown to $OD_{660}=0.1$. 3-Methylbenzylalcohol was then added to 3 mM for stimulating transcription from the Pu promoter. This extra step was included to eliminate background CelB remaining from stationary phase. Samples were removed at various time during growth for analysis of CelB or Luc activities.

For measurements of the CelB activities described in Table 2 cells were diluted 1000-fold after overnight growth and then grown to $OD_{660}=0.1$ before addition of the inducer. For analysis of amylose accumulation cells were grown in selective medium overnight, diluted 200-fold, and then grown further to $OD_{660}$=0.3–0.4. m-toluic acid was then added to 2 mM. Measurements of amylose accumulation (Brautaset et al., 1994, Microbiology, 140, 1183–1188) and CelB activities were performed 16 hours after addition of the inducer.

Preparation of cell-free extracts and measurements of phoshoglucomutase activities were performed as described by Fjærvik et al., (supra).

Measurements of luciferase activities were performed by using the Luciferase Assay System from Promega, and cell extracts were prepared from 90 µl cell culture, as described by the manufacturer. Samples were removed during growth and diluted or concentrated to $OD_{660}$=0.3 before preparation of the extracts. 10 µl of the cell extracts was used for the quantitation of light intensity by a scintillation counter.

Results

Construction of General Purpose Broad Host-range Cloning Vectors.

FIG. 1 outlines the procedures involved in constructing a set of relatively small RK2-based vectors with different antibiotic resistance markers (pJB3, pJB3Cm6, pJB3Tc20, and pJB3Km1). Plasmid pFF1 was used as a starting point for all the constructs, and many of the steps in the construction procedure served to delete unnecessary DNA sequences (size reduction), to eliminate undesired restriction endonuclease sites, or to create new such sites. One of the useful consequences of this is that the NdeI and SfiI sites in trfA were kept unique. All vectors share in common a polylinker/lacZ' region. Most of the restriction endonuclease sites in the polylinker region are unique, and the exceptions are caused by the presence of some of these sites in antibiotic resistance marker genes. All vectors contain oriT.

The complete nucleotide sequences of the vectors were established by combining sequences previously reported in the literature and by sequencing many of the junction sites involved in the construction procedures. This greatly simplifies the routine use of the vectors, further improvements, and generation of more specialized derivatives.

Vector Stability.

To improve plasmid stability for some hosts we inserted parDE into pJB3 generating pJB321, as shown in FIG. 1. To simplify stability measurements the xylE' fragment from pJB109 was also inserted into the polylinker of pJB3 and in pJB321, generating plasmids pJB3E and pJB321E, respectively. The fragment was inserted in such an orientation that xylE' could be transcribed from the lac promoter in the vector. FIG. 2 demonstrates the stabilizing effects of the parDE sequences in three different species. In *E. coli* the unmodified plasmid (pJB3E) is relatively stable, but in the presence of parDE (pJB321E) virtually no plasmid loss was observed (FIG. 2A).

As can be seen from FIG. 2B pJB321E is much more stable than pJB3E, illustrating the usefulness of this vector modification for certain hosts. In *Pseudomonas aeruginosa* the stability difference between the two plasmids was marginal (FIG. 2C), but the frequency of plasmid loss is so low in both cases that for most purposes practical problems should not be experienced.

Construction of Broad Host-range Expression Vectors.

Plasmid pJB7 was used as a starting point for the construction of expression vectors pJB137 and pJB653, containing the Pu and Pm promoters, respectively (FIG. 3). In the first steps the genes encoding the positive regulators XylR and XylSArg41Pro were inserted. The mutant gene xylSarg41pro was used because it causes a reduction of the level from Pm, compared to wild type xylS (Michan et al., supra). The Pu and Pm promoters were then inserted, generating plasmids pJB134 and pJB64. The remaining steps up to the final constructs pJB137 and pJB653 served to fill in undesired restriction endonuclease sites, to create new sites, and to insert a bidirectional transcriptional terminator between the Pu/Pm promoters and the trfA gene. This terminator has previously been shown to function in a wide variety of Gram-negative species (Fellay et al., supra and Frey and Krisch, supra). To simplify the routine use of these expression vectors they contain a polylinker region downstream of the Pu/Pm promoters (FIG. 3). In analogy to pJB321 (FIG. 1) the parDE region was also inserted into each of the constructs, generating pJB139 and pJB654 (Table 1).

Expression of the *Acetobacter xylinum* Phosphoglucomutase Gene, celB, from the Pu and Pm Promoters.

The 1.9 kb BamHI celB fragment from pUC7celB was cloned in an orientation that allowed transcription of the gene from Pu in pJB137 and Pm in pJB653, generating pJB137celB and pJB653celB. The expression levels were then monitored as a function of cell growth (FIG. 4A). As can be seen, the Pu promoter expresses very low levels of phosphoglucomutase in the absence of inducer as long as the cells are kept growing exponentially. The expression level in the presence of inducer is also low, but several fold higher than in uninduced cells. As the cells enter stationary phase the expression levels in the uninduced and induced cells increases strongly, although the induced cells express much more of the enzyme.

FIG. 4B shows the results of a corresponding expression study of pJB653celB, containing the Pm promoter. Expression from Pm does not seem to be affected significantly by the stage of growth but leakage and maximum expression are higher than for Pu. The results demonstrate that the leakage expression of this promoter is not growth phase dependent, and that the background level of expression is much higher than in exponentially growing cells containing pJB137celB (see legend to FIG. 4). As subsequent experiments show, this backward expression is sufficiently low not to cause a problem. Moreover, if necessary to reduce leakage (uninduced) expression, a down mutant of the Pm promoter could be used (Kessler et al., supra). Stimulation of the Pm promoter resulted in much higher expression levels of CelB than from Pu. For unknown reasons the levels of phosphoglucomutase dropped significantly at prolonged incubation levels, in contrast to what was observed in the experiments with the Pu promoter.

The copy numbers of the vectors were increased by exchanging the SfiINdeI fragment internally in the trfA gene. We have done this in pJB653celB and pJB137celB to analyse the copy number effects on celB expression (Table 2). For the Pu promoter in pJB137 the cop271C mutation leads to an increase in celB expression both in the absence and presence of inducer, and the magnitude of the increase is approximately proportional to the increase in copy number. (Haugen et al., 1992, supra). Surprisingly, however, when the copy number was increased further (about 20-fold) using cop254D (Haugen et al., 1992, supra) expression levels did not increase beyond the levels of cop271C. For the Pm promoter leakage expression increased strongly by introduction of the cop mutations, while the cop254D mutant expressed even less phosphoglucomutase than cop271C.

The effects of the cop254D mutation on expression was rather puzzling, but we believe that the results may at least partly be caused by a poisoning effect on the cells mediated by the high copy number of cop254D (Haugan et al., 1995, supra). We observed directly that the PGM1 strain containing this mutant was somewhat inhibited in its growth rate, while such an effect was not observed in another *E. coli* strain, DH5α. As can be seen from Table 2, the expression levels of phosphoglucomutase for the cop254D/Pm combination were much higher in DH5α than in PGM1. These results thus strengthen the hypothesis that cop-mutant mediated cell poisoning effects may influence strongly the expression from Pm.

Use of pJB6S3celB for Studies of Effects of celB Expression on Amylose Accumulation in *E. coli*.

FIG. 5 demonstrates that when cells are grown on maltose as carbon source amylose accumulates in similar quantities as cellular protein in PGM1. In the presence of a low level of expression of celB (uninduced state of Pm) amylose accumulation is only slightly affected. In other words, the leakage synthesis is not sufficiently high to block amylose accumulation, illustrating that this promoter system can be used to analyse rate-limiting steps in metabolic pathways. In the presence of inducer amylose accumulation is strongly reduced, as expected, in response to the increase in the intracellular phosphoglucomutase level. However, we found it surprising that a significant accumulation still takes place in spite of the presence of very high levels of phosphoglucomutase. We believe that this effect is somehow the result of the particular biochemical properties of the *Acetobacter xylinum* phosphoglucomutase enzyme. This is clearly illustrated by the observation that the phosphoglucomcase positive parent strain of PGM1 Hfr3000, does not accumulate measurable quantities of amylose (Brautaset, supra), even though the activity levels of the enzyme is as low as about 2% of the CelB activity under induced conditions (data not shown). This test system therefore seems to illustrate a case where a metabolic process can be modified by replacing an enzyme in a given host by a heterologous variant of the same enzyme.

Construction of an ATG Vector and Its Use to Study Luciferase Expression in *E. coli*, *X. campestris* and *P. aeruginosa*.

The DNA fragments containing the Pu/Pm promoters in pJB137/pJB653 both contain the ribosome-binding site. In addition, these fragments include for Pm the 5' terminal part of the first gene from the meta-cleavage pathway operon (Inouye et al., 1984, Gene, 29, 323–330) and for Pu the 5' terminal part of an ORF that has not been identified upstream of the first gene in the upper pathway operon (Harayama et al., 1989, J. Bacteriol. 171, 5048–5055; Inouye et al., 1984, Proc. Natl. Acad. Sci. 84, 1688–1691). This means that during expression of celb translation is probably first initiated at the natural signal sequences, and then reinitiated at the corresponding elements from *A. xylinum*. In order to create a more well-defined expression system we modified the region downstream of Pm in pJB653 such that the sequences downstream of the translation initiation ATG were eliminated, and new genes can be cloned directly in this ATG site after digesting the vector with AflIII (same cohesive ends as NcoI). AflIII was chosen since there is a NcoI site in the vector. The new vector was designated pJB653ATG (FIG. 6). The luc gene from the firefly was then inserted at the ATG site, generating plasmid pJB653ATGluc (Table 1). This plasmid was then used to monitor luc expression in *E. coli*, *X. campestris* and *P. aeruginosa*. Our data based on expression of luc in pJB653ATG, show that it is possible to obtain more than a 100-fold induction level in *X. campestris*. FIG. 7A shows that the kinetics of activation in *E. coli* were similar to that of celB (FIG. 4B), but the Luc activity was more stably maintained than the CelB activity upon prolonged incubation. Another difference is that the maximal ratio between the induced and uninduced state was significantly higher (between 300 and 400 fold) with pJB653ATGluc than with pJB653celB (between 50 and 100 fold). It is not clear whether this effect is somehow caused by the use of different reporter enzymes or by the changes introduced in the sequences downstream of the Pm promoter.

To quantitatively compare luc gene expression with some well-known expression vector we subcloned the luc gene at the ATG in the commercially available *E. coli* vector pTrc99A, generating pTrc99Aluc (Table 1). These experiments showed that the Luc activity in such cells (after IPTG induction) was similar to the activities in induced cells containing pJB653ATGluc, while the induction ratio was much lower from pTrc99A (Table 3). The high levels of expression from the induced Pm promoter were unexpected, because the copy number of the RK2 replicon is much lower than that of pTrc99A, and also because ptrc is known to be a very strong promoter. Pm has to our knowledge not been evaluated in this respect. To analyse these results further we inserted the cop271C mutation into the trfA gene of pJB653ATGluc and then repeated the expression experiments. The expression levels were much higher from this construct and exceeded the levels expressed from pTrc99A by a factor of seven. These data indicate that the Pm promoter may be useful for the purpose of maximizing gene expression.

To study the performance of pJB653ATGluc in a non-enteric host we transferred the plasmid to *X. campestris*, and measured luc expression in a similar way as in *E. coli*. FIG. 7B demonstrates that as in *E. coli* luc expression is very low in uninduced cells, while the activity increases more than 100-fold nine hours after induction. FIG. 7C illustrates luc expression in *P. aeruginosa*, in which the maximum luc expression level was achieved 12 hours after induction, resulting in a 120-fold induction ratio. It can therefore be concluded that pJB653ATGluc has a broad potential for expression studies in bacteria.

TABLE 1

Bacterial strains and plasmids used in Example 1[a]

| Bacterial strain or plasmid | Properties | Reference |
| --- | --- | --- |
| *Escherichia coli* | | |
| DH5α | endA1 hsdR17 supE44 thi-1 λ gyrA96 relA1 ΔlacU169 (φ80dlacZΔM15) | Bethesda Research Laboratories |
| S17.1 | RP4 2-T::Mu-Km::Tn7 pro res mod[+] | 1 |
| PGM1 | pgm derivative of Hfr3000 | 2 |

TABLE 1-continued

Bacterial strains and plasmids used in Example 1[a]

| Bacterial strain or plasmid | Properties | Reference |
|---|---|---|
| *Pseudomonas aeruginosa* | | |
| PAO1161S | Spontaneous streptomycin resistant derivative of PAO1161 | 3 |
| *Azotobacter vinelandii* | | |
| UW | Wild type | 4 |
| *Xanthomonas campestris* | | |
| B100-152 | Spontaneous exopolysaccharide mutant. | 5 |
| Plasmids | | |
| RK2 | 60 kb broad-host-range plasmid originally isolated from *Klebsiella aerogenes* Ap$^r$.Km$^r$.Tc$^r$. | 6 |
| pFF1 | RK2 minimal replicon Ap$^r$.Cm$^r$.5.9 kb. | 7 |
| pJB2 | Derivative of PFF1 where the EcoR1, BglII, and SalI sites were filled in by three steps. Ap$^r$.Cm$^r$.5.9 kb. | This work. |
| pUC19 | ColE1 replicon Ap$^r$.2.7 kb. | 8 |
| PUC19-3 | Derivative of PUC19 where the NdeI site was filled in (step 1) and the SspI and AflIII sites flanking the lac region were converted to NsiI and BglII (steps 2 and 3, respectively). Ap$^r$.2.7 kb. | This work. |
| pJB5 | Derivative of PJB2 where 0.5 kb of the upstream part of the Cm resistance gene was deleted with PvuII digestion, followed by insertion of a BglII linker at the same site (step 1). Two DamH1 sites flanking Pneo were also filled in (step 2) Ap$^r$. 5.4 kb. | This work |
| pKH3 | Derivative of pJB5 where 0.7 kb PstI/BqlII fragment was replaced with a 1.O kb MsiI/BglII fragment containing the polylinker and lac regions from pUC19-3. Ap$^r$.5.7 kb. | This work |
| pJB7 | Deletion derivative of pJB5 obtained by digestion with AflIII + Eco47III (0.4 kb, step 1) and NotI + partial AccI digestion (0.5 kb, step 2) Ap$^r$. 4.5 kb. | This work |
| pJB3 | Derivative of pJB7 where 1.5 kb BglII/SfiI fragtnent was replaced with a 1.8 kb BglII/SfiI fragrnent containing the polylinker and lac regions from pKH3. Ap$^r$. 4.8 kb. | This work |
| pRR120 | pBluescript II SK(+) with 0.8 kb parDE region from RK2. Ap$^r$. 3.8 kb. | 9 |
| pJB9 | Derivative of pRR120 where the polylinker sites between HindIII and SmaI, downstream of parDE, were deleted by digestion with HindIII (filled in) and SmaI. Ap$^r$. 3.8 kb. | This work |
| pJB10 | Derivative of pJB9 where the KpnI site upstream of parDE was converted to BglII. Ap$^r$. 3.8 kb. | This work |
| pHL12 | Derivative of pJB9 where the BamHI site downstream of parDE was filled in (step 1), and the KpnI site upstream of parDE converted to XbaI (step 2) Ap$^r$. 3.8 kb. | This work |
| pJB313 | Derivative of pJB3 where 0.8 kb BglII/BamHI fragment containing the parDE fragment from pJB10 was inserted into the BglII site. Ap$^r$. 5.6 kb. | This work |
| pJB321 | Same as pJB313, except that the parDE fragrnent is in the opposite orientation. | This work |
| pαxy1Ω | RSFIO10 replicon, Cm$^r$. 13.2 kb. | 10 |
| pUC7 | ColE1 replicon. Ap$^r$ 2.7 kb. | 11 |
| pJB107 | Derivative of PUC7 where the promoterless xylE gene frotn pαxy1EΩ | This work |

TABLE 1-continued

Bacterial strains and plasmids used in Example 1[a]

| Bacterial strain or plasmid | Properties | Reference |
|---|---|---|
| | was cioned as a 2.0 kb BamHI fragment into pUC7 digested with the satne enzyme. Ap[r]. 4.7 kb. | |
| pJB109 | Derivative of PJB107 where the two SacII sites fianking the xy1E gene in pJB107 was converted to EcoRI sites (step 1). This 1.2 kb EcoRI fragment (here noted XY1E') was then cioned into PUC7 digested with EcoRI (step 2). Ap[r]. 3.9 kb. | This work |
| pJB3E | Derivative of pJB3 where the 1.2 kb EcoRI xylE' fragment from pJB109 was cioned into the polyiinker EcoRI site in PJB3. Ap[r]. 6.0 kb. | This work |
| pJB313E | Derivative of pJB313 where the 1.2 kb EcoRI xylE' fragment from pJB109 was cloned into the poiylinker EcoRI site in pJB313. Ap[r]. 6.8 kb. | This work |
| pJB321E | Derivative of pJB321 where the 1.2 kb EcoRI xylE' fragment from pJB109 was cloned into the polylinker EcoRI site in pJB321. Ap[r]. 6.8 kb. | This work |
| pSV16 | RK2 repiicon. Ap[r]. Km[r]. 3.3 kb. | 12 |
| pJB3Km1 | Derivative of pJB3 where the Km resistance gene of PSV16 was inserted into the BgIII site as an 1.2 kb BamHI fragment. Ap[r]. Km[r]. 6.1 kb. | This work |
| pJB3Km2 | Same as pJB3Km1, except that the Km resistance gene was cloned in the opposite orientation. | This work |
| pUC7TC | Derivative of pUC7 where the Tc resistance gene of RK2 was cloned as a 2.3 kb blunt-ended StuI/BglII fragment into the HincII site of pUC7. Ap[r]. Tc[r]. 5.0 kb. | This work |
| pJB3Tc20 | Derivative of pJB3 where the Tc resistance gene frotn pUC7Tc was inserted as a 2.3 kb BamHI fragment into the BgIII site. AP[r]. Tc[r]. 7.1 kb. | This work |
| pJB3Tc19 | Same as pJBTc201 except that the Tc resistance gene was cloned in the opposite orientation. | This work |
| pUC7Cm | Derivative of PUC7 where the Cm resistance gene was cloned as a 1.4 kb PstI/HgiAI blunt-ended fragment from pFF1 into the HincII site of PUC7. Ap[r]. Cm[r]. 4.1 kb. | This work |
| pJB3Cm6 | Derivative of pJB3 where the Cm resistance gene of pUC7Cm was cloned as an 1.4 kb BamHI fragment into the BgIII site. Ap[r]. Cm[r]. 6.2 kb. | This work |
| pJB3Cm10 | Same as pJB3Cm6, except that the Cm resistance gene was cloned in the opposite orientation. | This work |
| pJB8 | Derivative of pJB7 where the NcoI site was converted to EcoRI. Ap[r]. 4.5 kb. | This work |
| pERD839 | RSF1010 replicon containing xy1S839. Km[r]. Sm[r]. 14.7 kb | 13 |
| pJB86 | Derivative of pJB8 where xy1S839 was cloned as a 1.7 kb B&mHI fragment from pERD839 into the BgIII site. The xy1S839 gene is transcribed in the same direction as the bla and trfA gene. Ap[r]. 6.2 kb. | This work |
| pERD21 | RSF1010 replicon containing the Pm promoter. Km[r]. 13.8kb. | 14 |
| pUC129 | ColE1 replicon. Ap[r]. 3.3 kb. | 15 |
| pJB103 | pUC129 with Pm promoter cloned as an 0.6 kb EcoRI/PvuII fragment from PERD21 into the EcoRI/EcoRV-digested vector. Ap[r]. 3.9 kb. | This work |
| pJB64 | Derivative of pJB86 where the Pm promoter was cloned as an 0.6 kb NsiI/ EcoRI fragment from pJB103 into pJB86 | This work |

TABLE 1-continued

Bacterial strains and plasmids used in Example 1[a]

| Bacterial strain or plasmid | Properties | Reference |
|---|---|---|
| | digested with PstI and EcoRI. Ap[r]. 6.8 kb. | |
| pJB651 | Derivative of pJB64 where the orientation of Pm was reversed by digestion with KpnI followed by religation (step 1). A series of restriction endonuclease sites upstream of Pm were eliminated by HindIII and EcoRI digestion (step 2), and downstream of Pm by SalI and BamHI digestion (step 3). The remaining KpnI site downstream of pm was converted to a HindIII site (step 4) Ap[r]. 6.8 kb. | This work |
| pJFF350 | ColE1 replicon containing transcriptional terminators of the Ω-Km transposable element. Km[r]. 5.3 kb. | 16 |
| pJBI7 | Derivative of pUC19 where the XbaI site in the polylinker was filled in (step 1), and the polylinker PstI site was converted to XbaI (step 2). Ap[r]. 2.7 kb. | This work |
| p7B1725 | The 3.6 kb blunt-ended HindIII fragment containing the Ω transcriptional terminators and the Km resistance gene from pJFF350 was cloned into the HincII site of pJB17 (step 1). The Km and ori region (3.0 kb) from pBR322 was deleted by StyI digestion (step 2). Ap[r]. 3.3 kb. | This work |
| pJB1726 | The XbaI site in pJB1725 was converted to a HindIII site. Ap[r]. 3.3 kb. | This work |
| pJB652 | Derivative of pJB6S1 where the Ω transcriptional terminators of pJB1726 were cloned as an 0.6 kb HindIII/EcoRI fragment into pJB651 digested with the same enzymes. Ap[r]. 7.4 kb. | This work |
| pJB653 | Derivative of pJB652 where the PstI fragment containing the Pm promoter was cloned in the opposite direction by digesting pJB652 with PstI followed by religation. This step was necessary since DNA sequencing showed that Pm was in the incorrect orientation in pJB652. Ap[r]. 7.4 kb. (It should be noted that although xylS was cloned from pERDB39, sequencing data indicates that pJB6S3 contains wild-type xylS- this is reflected in FIG. 6.) | This work |
| pJB654 | The XbaI site upstream parDE in pJB139 and the BbsI site upstream xy1S939 in pJB653 were filled in (step 1) Originally, there were two XbaI sites and two DbsI sites flanking parDE and xy1S839, respectively. The 3.0 kb SfiI/BbsI (BbsI made blunt) fragment of pJB6S3 was replaced with the 3.B kb SfiI/XbaI (XbaI made blunt) parDE containing fragment from pJB139. Ap[r]. 8.2 kb. | |
| pTS174 | pACYC184 replicon, carries xylR. Cm[r]. | 17 |
| pJB101 | Derivative of pUC7 where a 2.4 kb xylR-containing HpaI fragment was cloned into the polylinker HincII site of pUC7. Ap[r]. 5.1 kb | This work |
| pJB13 | Derivative of pJB8 where the xy1R gene of pJB101 was cloned as a 2.4 kb BamHI fragment into the BglII site of pJBB. The xy1R gene is transcribed in the same direction as the bla and trfA gene. Ap[r]. 6.9 kb. | This work |
| pRD579 | R1 replicon, carries the Pu promoter. Cb[r]. | 18 |
| pUC18 | ColE1 replicon. Ap[r]. 2.7 kb. | 8 |
| pJB105 | Derivative of PUC18 where the Pu promoter was cloned as an 0.3 kb EcoRI/ | This work |

TABLE 1-continued

Bacterial strains and plasmids used in Example 1[a]

| Bacterial strain or plasmid | Properties | Reference |
|---|---|---|
| | BamHI fragment from pRD579 into PUC18 digested with the same enzymes. Ap[r]. 3.0 kb. | |
| pJB134 | Derivative of pJB13 where the Pu promoter was cloned as an 0.4 kb EcoRI/PstI fragment from pJB105 into pJB13 digested with the same enzymes. Ap[r]. 7.0 kb. | This work |
| pJB136 | Derivative of pJB134 where the EcoRI site upstream of the Pu promoter was filled in (step 1) and the BamHI site downstream of Pu was converted to EcoRI (step 2). Ap[r]. 7.0 kb. | This work |
| pJB137 | Derivative of pJB136 where the Ω transcriptional terminators from pJB172S were cloned as an 0.6 kb EcoRI/XbaI fragment into pJB136 digested with the same enzymes. Ap[r]. 7.6 kb. | This work |
| pJB139 | Derivative of pJB137 where the XbaI site was filled in (step 1) and the TthI Site converted to XbaI (step 2). The parDE fragment from PHL12 was inserted into the XbaI site as a 0.8 kb XbaI fragment (step 3). The parDE gene is transcribed counterclockwise to the xylR gene. Ap[r]. 8.4 kb. | This work |
| pTB16 | ColE1 replicon. Ap[r]. 4.3 kb. | 19 |
| pUC7celB | Derivative of PUC7 where the 1.9 kb blunt-ended SphHI celB fragment from pTB16 was cloned onto the HincII site of pUC7. Ap[r]. 4.6 kb. | This work |
| pJBl37celB | Derivative of pJB137 where the 1.9 kb BamHI celB fragment from pUC7celB was cloned in pJB137 digested with the same enzyme. celB is transcribed from the Pu promoter. Ap[r]. 9.5 kb. | This work |
| pJB653celB | Derivative of pJB653 where the 1.9 kb BamHI celB fragment from pUC7celB was cloned in pJB653 digested with the same enzyme. celE is transcribed from the Pm promoter. Ap[r]. 9.3 kb. | This work |
| pFF1cop254D | pFF1 containing the cop254D mutation. Ap[r]. Cm[r]. 5.9 kb. | 3 |
| pFF1cop271C | pFF1 containing the cop271C mutation. Ap[r]. Crflr. 5.9 kb. | 20 |
| pJB137celBcop254D | Derivative of pJB137celB where the 0.6 kb NdeI/SfiI fragment was replaced with the 0.6 kb NdeI/SfiI fragment from pFFIcop254D containing the cop254D mutation. Ap[r]. 9.5 kb. | This work |
| pJB137celBcop271C | Derivative of pJB137celB where the 0.6 kb NdeI/SfiI fragment was replaced with the 0.6 kb NdeI/SfiI fragment from pFFlcop271C containing the cop271C mutation. Ap[r]. 9,. kb. | This work |
| pJB653celBcop254D | Derivative of pJB6s3celB where the 0.6 kb NdeI/SfiI fragment was replaced with the 0.6 kb NdeI/SfiI fragment from pFFlcop254D containing the cop2S4D mutation. Ap[r]. 9.3 kb. | This work |
| pJB653celBcop271C | Derivative of pJB653celB where the 0.6 kb NdeI/SfiI fragment was replaced with the 0.6 kb NdeI/SfiI fragment from pFFlcop271C containing the cop271C mutation. Ap[r]. 9.3 kb. | This work |
| pGEM-luc | pGEM-luc contains the luc gene encoding firefly luciferase. | Promega Ap[r]. 4,9 kb. |
| pTrc99A | Expression vector containing the trc promoter. ColE1 replicon. Ap[r]. 4.2 kb. | Pharmacia LKB Biotechnology |

TABLE 1-continued

Bacterial strains and plasmids used in Example 1[a]

| Bacterial strain or plasmid | Properties | Reference |
|---|---|---|
| pTrc99Aluc | Derivative of pTrc99A where the luc gene from pGEM-luc was cloned as a 1.7 kb NcoI/BamHI fragment arnplified by PCR into pTrc99A digested with the same enzymes. Ap[r]. 5.9 kb. | This work |
| pJB653ATG | ATG expression vector. A derivative of pJB653 where the 413 bp EcoR1/PstI fragment containing the Pm proi#oter is replaced with a 139 bp EcoRI/PstI fragment containing Pm and an AflIIII site. Ap[r]. 7.2 kb. | This work |
| pJB653ATGluc | The luc gene from PGEM-luc was cloned as a 1.7 kb NcoI/BamHI fragment into the AflIIII/BaznHI site of pJB653ATG. Ap[r]. 8.9 kb. | This work |
| pJB653ATGluccop271C | Derivative of pJB653ATG1uc where the 1.5 kb BamHI/SfiI fragment was replaced with the 1.5 kb BaniHI/StiI fragment from pJB653celBcop271C. Ap[r]. 8.9 kb. | This work |

[a]Ap[r], ampicillin resistance; Cm[r], chloramphenicol resistance; Km[r], kanamycin resistance; Tc[r], tetracycline resistance; Cb[r], carbenicillin resistance.

1. Simon. R. U. Priefer and A. Pühler, 1983, Bio/Technology, 1, 784–791.
2. Adhya, S. and M. Schwartz, 1971, J. Bacteriol, 108, 621–262.
3. Haugan, K., Karunakaran, P., Trondervik A. and Valla S., 1995, Plasmid, 33, 27–39.
4. Bishop, P. E. and Brill, W., 1977, J. Bacteriol, 130, 954–956.
5. Hötte, B., Rath-Arnold, I., Pühler, A. and Simon R., 1990, J. Bacteriol, 172, 2804–2807.
6. Ingram, L. C., Richmond, M. H. and Sykes R. B., 1973, Agents Chemoter, 3, 279–288.
7. Durland, R. H., Toukdarian, A., Fang. F. and Helinski, D. R., 1990, J. Bacteriol, 172, 3869–3867.
8. Norrander, J., Kempe, T. and Messing, J., 1983, Gene, 26, 101–106.
9. Roberts, R. C. and Helinski, D. R., 1992, J. Bacteriol, 174, 8119–8132.
10. Frey, J., Mudd, E. A. and Krisch, H. M., 1988, Gene, 62, 237–247.
11. Vieira, J. and Messing J., 1982, Gene, 19, 259–268.
12. Valla, S., Haugan, K., Durland, R. H. and Helinski, D. R., 1991, Plasmid, 25, 131–136.
13. Michan, C., Zhou, L., Gallegos, M., Timmis, K. N. and Ramos, J., 1992, J. Biol. Chem., 267, 22897–22901.
14. Ramos, J. K., Gonzalez-Carrero, M. and Timmis, K. N., 1988, FEBS Letters, 226, 241–246.
15. Keen, N. T., Tamaki, S., Kobayashi, D. and Trollinger, D., 1988, Gene, 70, 191–197.
16. Fellay, R., Krisch, H. M., Prentki, P. and Frey, J., 1989, Gene, 76, 215–226.
17. Inouye, S., Nakazawa, A. and Nakazawa, T., 1983, J. Bacteriol., 155, 1192–1199.
18. Dixon, R., 1986, Molec. Gen. Genet., 203, 129–136.
19. Brautaset, T., Standal, R., Fjærvik, E. and Valla, S., 1994, Microbiology, 140, 1183–1188.
20. Haugan, K., Karunakaran, P., Trøndevik, A. and Valla, S., 1995, Plasmid, 33, 27–39.

TABLE 2

CelB activities as a function of plasmid copy number in E. coli

| | | CelB activity (nmole/min/mg protein) | |
|---|---|---|---|
| Strain | t = 0 hours | uninduced[a] | induced[a] |
| PGM1 (pJB137celB) | 10 | 450 | 1300 |
| PGM1 (pJB137celBcop271C) | 90 | 1400 | 3500 |
| PGM1 (pJB137celBcop254D) | 100 | 1400 | 2800 |
| PGM1 (pJB653celB) | 200 | 250 | 13000 |
| PGM1 (pJB653celBcop271C) | 4000 | 2000 | 30000 |
| PGM1 (pJB653celBcop254D) | 4000 | 1000 | 9000 |
| DH5α (pJB6S3celB) | 450 | 360 | 15300 |
| DH5α (pJB653celBcop254D) | 15300 | 14000 | 59100 |

[a]Cells were harvested 4 (pJB653celB) or 6 (pJB137celB) hours after induction.

TABLE 3

Luc activity as a function of plasmid copy number in E. coli DH5α

| | | Luc activity (cpm × 10⁶) | | |
|---|---|---|---|---|
| plasmid | # hours[a] | uninduced | induced | ratio |
| pJB653ATGluc | 3 | 1.1 | 170 | 155 |
| pJB653ATGluc | 5 | 1.7 | 670 | 394 |
| pJB653ATGluccop271C | 3 | 7.5 | 1400 | 187 |
| pJB653ATGluccop271C | 5 | 14 | 3500 | 250 |
| pTrc99Aluc | 3 | 48 | 540 | 11 |
| pTrc99Aluc | 5 | 34 | 520 | 15 |

[a]t = 0 hours at induction

EXAMPLE 2

Materials and Methods

In this Example the expression from Pm, of three genes, luc, celB, and cat, encoding chloramphenicol acetyltranferase (CAT) was compared in E. coli, X. campestris and P.

Aeruginosa. The trfA mutation designated cop251M has been previously isolated by Durland et al., 1990 (supra) and has also independently been isolated by us. This copy up mutant was cloned into the expression vector pJB653ATG (see Example 1), using techniques as described in Example 1, generating pJB653ATGcop251M. Further following the procedures of Example 1, the luc gene was inserted into pJB653ATGcop251M, generating pJB653ATGluccop251M.

As a comparison, plasmid pT7-7(1.9) was constructed, in which celB was cloned into pT7-7 (United States Biochemical Corporation (USB), Cleveland, Ohio, USA; Tabor and Richardson, 1985, Proc. Natl. Acad. Sci. USA, 262, 1074–1078) as a 1.9 kb NdeI/PstI PCR fragment into the NdeI and PstI sites of pT7-7. The fragment for cloning was prepared by PCR techniques using standard methods. An NdeI site at the ATG in CelB was created in a PCR reaction using appropriately modified primers.

Plasmids pJB653ATGluc, pJB653ATGluccop271C, pTrc99Aluc, pJB653ATGcelB, pJB653ATGcelBcop271C were as prepared in Example 1.

The vector pJB653ATGcat was constructed as follows: cat was cloned as a 662 bp NcoI BamHI fragment from pCat3Basic (from Promega) into AflIII/BamHI in pJB653ATG (obtained according to Example 1). First, the XbaI site downstream cat in pCat3Basic was converted to a BamHI site by the use of a BamHI linker (NEB) after making the XbaI site blunt by Klenow. The comparative vector pTrc99Acat was constructed as follows: cat was cloned as a NcoI/BamRI fragment (as above) into NcoI/BamHI in pTrc99A.

Expression studies All strains were grown as described in Example 1. Transcription from Pm was induced by 2 mM or 0.5 mM m-toluic acid in E. coli and X. campestris, respectively. 0.25 mM IPTG was used for induction of expression from the pTrc promoter. The strain containing pT7-7(1.9) was grown in LB medium+ampicillin+kanamycin overnight at 30° C. The cells were diluted 50-fold and grown further for 3 hours. Cells containing the Pm vectors were diluted 100-fold. celB expression was induced by heat at 42° C. for 30 minutes and the cells were grown for another 1.5 hours at 30° C. Preparation of cell-free extracts and measurements of phosphoglucomutase and luciferase activities are described in Example 1. The preparation of cell extracts for chloramphenicol acetyltransferase activities were performed as described by Sambrook et al., 1989, supra (a modified version); 1) Cells were harvested from 1 ml culture by centrifugation at 12000 g, 1 minute at 4° C. 2) The cell pellets were resuspended in 100 μl of freshly prepared 1 mg/ml egg white lysozyme, 200% sucrose, 30 mM Tris-Cl pH 8.0, 1 mM EDTA pH 8.0. On ice for 10 minutes. 3) Lysis was completed by freezing/thawing in liquid $N_2$/37° C. (2×). In case of deacetylases in the cell extract, the extracts were incubated at 650 for 10 minutes, followed by centrifugation at 12000 g for 10 minutes. CAT activity was measured according to the protocol of the QUAN-T-CAT assay system from Amersham Life Science.

Results

The results are presented in Tables 4, 5 and 6. It will be seen that in addition to luc and celB, the cat gene may also be expressed from the expression vectors of the invention, at significant levels of expression (Table 5). These data indicate that the Pm promoter is a strong system for expression. Table 4 shows that luc expression was even better in Pseudomonas as compared with E. coli. Luc is better expressed from a wild-type trfA vector in Pseudomonas, than from cop mutants in E. coli, suggesting that there is a potential for further improvement in expression in Pseudomonas. In the case of cat expression, expression in Pseudomonas with wild-type trfA is better than in E. coli, but not with cop mutants.

TABLE 4

Measurements of Luc activity in E. coli, P. aeruginosa, and X. campestris

| strain/plasmid | # hours[a] | Luc activity cpm × $10^6$ uninduced | induced |
|---|---|---|---|
| E. coli DH5α | | | |
| pJB653ATGluc | 5 | 2 | 560 |
| pJB653ATGluccop271C | 5 | 35 | 3400 |
| pJB653ATGluccop251M | 5 | 94 | 5000 |
| pTrc99Aluc | 5 | 34 | 520 |
| Xanthomonas campestris B100-152 | | | |
| pJB653ATGluc | 21 | 0.6 | 240 |
| Pseudomonas aeruginosa PAO1161S | | | |
| pJB653ATGluc | 12 | 51 | 6200 |

[a]t = 0 hours at induction

TABLE 5

Measurements of CAT activity in E. coli, P. aeruginosa, and X. campestris

| Strain/plasmid | # hours[a] | CAT activity dpm × $10^6$ uninduced | induced |
|---|---|---|---|
| E. coli DH5α | | | |
| pJB653ATGcat | 5 | 0.14 | 32 |
| pJB6s3ATGcatcop271C | 5 | 2 | 62 |
| pJB653ATGcatcop251CM | 5 | 7 | 270 |
| pTrc99Acat | 5 | 130 | 140 |
| Xanthomonas campestris B100-152 | | | |
| pJB653ATGcat | 16 | 0.03 | 0.85 |
| Pseudoinonas aeruginosa PAO1161S | | | |
| pJB653ATGcat | 12 | 0.79 | 78 |

[a]t = 0 hours at induction

TABLE 6

Measurements of CelB activity in E. coli

| strain/plasmid | # hours[a] | CelB activity[b] (nmole/min/ mg protein) uninduced | induced |
|---|---|---|---|
| E. coli DH5α | | | |
| pJB653ATGcelB[d] | 5 | 1920 | 138000 |
| pJB653ATGcelBcop271C | 5 | 12850 | 329000 |

TABLE 6-continued

Measurements of CelB activity in *E. coli*

| strain/plasmid | # hours[a] | CelB activity[b] (nmole/min/ mg protein) uninduced | induced |
|---|---|---|---|
| pJB653ATGcelBcop251M PGM1 pT7-7 (1.9) | 5 | 62300 nd[c] | 455500 445000 |

[a] t = 0 hours at induction
[b] Preparation of cell extracts: 10 ml cell culture was resuspended in 3 ml 40 mM imidazol-HCl pH 7.4 before sonication expr. For pT7-7(1.9), 5 ml cell culture was resuspended in 3 ml 40 mM imidazol-HCl pH 7.4.
[c] nd = not determined in this experiment, but previous results have shown that the uninduced state is approximately 50% lower than induced state.
[d] The pJB653ATG vector used for expression of celB is not the same as used for luc and cat expression analysis. The vector used for celB expression bas an NdeI site in the ATG start site and not an AflIII site. The vector suitable for celB expression may be produced as follows: The PstI site upstream of the polylinker in pJB653NdeI-A (see Table 7) was made blunt, and the HindIII/SfiI fragment of pJB653NdeI-A was replaced by the 848-bp HindIII/SfiI fragment containing the trfA gene from pTBtrfA2. The PstI site (originally from the HindIII/SfiI fragment of pTBtrfA2) was made blunt. Ap[r]. 6.8kb. pTBtrfA2 was produced as follows: trfA was cloned as a 1.2 kb PstI/EcoRI fragment from pRD110-34 (Table 7) into the same sites in pALTER-1 (Table 7). The NdeI site in the trfA gene was eliminated by site-specific mutagenesis. TC[r]. 6.9 kb.

EXAMPLE 3

An SDS-PAGE (8% polyacrylamide) was performed on samples of protein expressed in *E. coli* DH5α from the "celB" vectors of Example 2, using standard procedures as described in Sambrook at al, supra, as follows:

| Sample | Protein conc. (mg/ml) | # μl extract loaded on gel |
|---|---|---|
| Wild-type trfA (wt) 0 mM | 0.65 | 8.2 |
| Wild-type trfA (wt) 2 mM | 0.53 | 10 |
| cop271C 0 mM | 0.72 | 7.4 |
| cop271C 2 mM | 0.53 | 10 |
| cop251M 0 mM | 0.76 | 6.9 |
| cop251M 2 mM | 0.56 | 9.5 |

The concentrations 0 mM and 2 mM refer to the inducer (see Example 2).

The results are shown in FIG. 8, which show celB expression as protein, rather than activity, from the various "CelB" vectors of Example 2.

EXAMPLE 4

The vector pJBSD1 was constructed in which in the vector pJB653ATG of Example 1, the location of trfA was altered such that it was deleted from its original location in pJB653ATG and placed downstream of the Pm promoter. pJBSD1 is shown in FIG. 9, and details of its construction are summarised in tabular form in Table 7 below, with reference to the following source plasmids:
Characteristics and References of the Plasmids Used in the Construction of pJBSD1
1. pJB653ATG—ATG expression vector (see Example 1).
2. pRD110-34—pBR322 replicon where an EcoRI/Pst fragment was substituted with the trfA gene from plasmid RD2. Durland et al., J. Bacteriol, 172, 3759–3867 (1990).
3. pALTER®-1—Mutagenesis vector used in the ALTERED SITES® II in vitro mutagenesis system. From Promega.
4. pSELECT™-1—Mutagenesis vector used in the ALTERED SITES™ in vitro mutagenesis system. From Promega.
5. pTB16—A plasmid carrying celB gene encoding phosphoglucomutase. Brautaset et al, Microbiology 140, 1183–1188(1994).

TABLE 7

Description of the plasmids used in the construction of pJBSD1

| | | |
|---|---|---|
| 1. | pJB653ATG - | ATG expression vector (see Example 1), Ap[r], 6.8 kb. |
| 2. | pJB653NdeI-A - | Derivative of pJB653ATG in which the AflIII site was converted to a NdeI site by replacing the 143 bp PstI/EcoRI fragment of pJB653ATG with the PstI/EcoRI PCR fragrnent containing the NdeI site, Ap[r], 6.8 kb. |
| 3. | pJB653NdeI-B - | Derivative of pJB653NdeI-A in which the PstI site upstream of the Pin promoter has been filled in, Ap[r], 6.8 kb. |
| 4. | pRD110-34 - | ColE1 replicon where EcoRl-Pst1 fragment of pBR322 was substituted with the trfA gene from plasmid RK2, TC[r], 4.8 kb. (Durland et al., J. Bacteriol., 172, 3759–3867 (1990).) |
| 5. | pALTER-1 - | Mutagenesis vector used in the ALTERED SITE ® IT in vitro mutagenesis system, TC[r], 5.7 kb. From Promega. |
| 6. | pALTERtrfA-1 - | trfA was cloned as a 1.2 kb PstI/EcoRI fragment from pRD110-34 into the sarne sites in pALTER-1, TC[r], 6.9 kb. |
| 7. | pALTERtrfA-NdeI - | Derivative of pALTERtrfA-1 in which the NdeI site in the trfA gene was eliminated by site specific mutagenesis, TC[r], 6.9 kb. |
| 8. | pJB653NdeIC2 - | Derivative of pJB653NdeI-B in which the 1.2-kb HindIII/SfiI fragment was replaced with the 1.2 kb HindIII/SfiI fragment from pALTERtrfA-NdeI, Ap[r], 6.8 kb. |
| 9. | pJB6S3NdeIC2b - | Derivative of pJB653NdeIC2 in which the PstI site has been filled in, Ap[r], 6.8 kb. |
| 10. | pSELECT -1 - | Mutagenesis vector used in the ALTERED SITES in vitro mutagenesis system, Tc[r], 5.7 kb. From Promega. |
| 11. | PTB16 - | A ColE1 replicon carrying celB gene encoding phosphoglucomutase, Ap[r], 4.3 kb. (Brautaset et al., Microbiology 140, 1183–1188 (1994).) |
| 12. | pSEL(1.9)B - | The celB gene from pTB6 was cloned as a 1.9 kb SphI fragment into the same site in pSELECT-1. NdeI site was made at the start codon of celB by site directed mutagenesis, Tc[r], 7.6 kb. |
| 13. | pJB653NdeIC2bCelB - | Derivative of pJB653NdeIC2b in which the celB gene from pSEL(1.9)B was cloned as a 1.9 kb NdeI/BamHI fragment into the sanie sites of pJB653NdeIC2b, Ap[r], 8.7 kb. |
| 14. | pJB653NdeIC2btrfA - | Derivative of pJB6S3NdeIC2bCelB in which the 1.9 kb NdeI/PstI fragment containing celB gene was replaced with a 1.2 kb MseI/PstI fragment containing the trfA gene, Ap[r], 8 kb. |
| 15. | pJBSD1 - | Derivative of pJB653NdeIC2btrfA in which the trfA gene downstream of |

TABLE 7-continued

Description of the plasmids used in the
construction of pJBSD1

Pneo promoter was deleted with
PvuII/HindIII digestion followed by
filling in and religation of the
vector part, Ap$^r$, 6.6 kb.

Ap$^r$ = ampicillin resistance
Tc$^r$ = tetracycline resistance

PJBSD1 was transferred to *E. coli* DH5α as described in Example 1, and the cells were grown in LB medium overnight at 30° C. in the presence of 1 mM toluate and 0.1 mg/ml of ampicillin. Some plates were incubated at 23° C. for 2 days. Cells were then diluted and plated on LB medium containing the ampicillin and toluate concentrations indicated in Table 8, at approximately 100 cells per plate. The plates were incubated at the temperatures indicated in Table 8 and the results are shown in Table 8. + means that colonies appeared after overnight incubation, while − means no growth.

Reading the data in the Table 8 horizontally, it will be seen that replication is controlled by the inducer level. It appears that slightly less inducer is required as the temperature is lowered; at 23° C. the plasmids appear to replicate even in the absence of inducer. The reason for this could be that Pm is better expressed, that the beta-lactamase is better expressed or more active, that the functionality of TrfA increases somewhat, or that the plasmid copy number increases slightly. Possibly, more TrfA is made at low temperatures or less is required for replication. Such TrfA expression at low temperatures could be dealt with by introducing mutations in Pm or its Shine-Dalgarno sequence, such that trfA expression is reduced. If Table 8 is read vertically, it will be noted that the ampicillin resistance level is affected by the inducer concentration, even at a fixed temperature. This must mean that as inducer concentrations are being lowered, trfA expression becomes reduced. This first leads to copy number reductions (reduced ampicillin tolerance) and then (no inducer) to total block of replication (no growth even at low ampicillin concentrations). The properties of vector pJBSD7 are thus remarkable and unique.

TABLE 8

Control of pJBSD1 replication by the externally added inducer m-Toluic acid

| Ampicillin concentration in | Toluic acid concentration in | 23° C. | | | | | 30° C. | | | | | 37° C. | | | | | 42° C. | | | | |
|---|---|---|---|---|---|---|---|---|---|---|---|---|---|---|---|---|---|---|---|---|---|
| mg/ml | mM | 0.0 | 0.1 | 0.5 | 1.0 | 2.0 | 0.0 | 0.1 | 0.5 | 1.0 | 2.0 | 0.0 | 0.1 | 0.5 | 1.0 | 2.0 | 0.0 | 0.1 | 0.5 | 1.0 | 2.0 |
| 0.1 | | + | + | + | + | + | − | + | + | + | + | − | − | + | + | + | − | + | + | + | + |
| 0.2 | | + | + | + | + | + | − | + | + | + | + | − | − | + | + | + | − | − | + | + | + |
| 0.4 | | + | + | + | + | + | − | + | + | + | + | − | − | + | + | + | − | − | − | + | + |
| 0.6 | | − | − | − | + | + | − | − | − | + | + | − | − | − | + | + | − | − | − | − | + |
| 0.8 | | − | − | − | − | − | − | − | − | − | − | − | − | − | − | − | − | − | − | − | − |

What is claimed is:

1. An expression vector comprising an RK2 minimum replicon, including a trfa sequence, together with an expression cassette comprising a promoter Pm and a xylS sequence from a TOL plasmid, and/or a promoter Pu and a xylR sequence from a TOL plasmid.

2. An expression vector as claimed in claim 1 wherein, in said RK2 minimum replicon, the trfa sequence is a copy-up (COP) mutant.

3. An expression vector as claimed in claim 1, wherein said RK2 minimum replicon carries mutations in the trifA sequence that are temperature-sensitive for replication.

4. An expression vector as claim in claim 1 wherein the trfa sequence is under control of a Pm and/or Pu promoter.

5. An expression vector as claimed in claim 1, comprising Pm and a xyls, xyls2tr6, or xylsarg41pro sequence.

6. An expression vector as claimed in claim 1, comprising a polylinker/lacZ' region.

7. An expression vector as claimed in claim 1, comprising an RK2-derived OriT.

8. An expression vector as claimed in claim 1, further comprising one or more further regulatory and/or enhancer elements.

9. An expression vector as claimed in claim 1, comprising a plasmid-encoded stability region.

10. An expression vector as claimed in 9, wherein said plasmid-encoded stability region comprises par loci.

11. A host cell containing an expression vector as defined in claim 1.

12. A host cell as claimed in claim 11, wherein said host cell is selected from the group consisting of Escherichia sp., Salmonella, Klebsiella, Proteus, Yersinia, Azotobacter sp., Pseudomonas sp., Xanthomonas sp., Caulobacter sp., Acinetobacter sp., Aeromonas sp., Agrobacterium sp., Alcaligenes sp., Bordatella sp., Haemophilus Influenzae, *Methylophilus methylotrophus*, Rhizobium sp., Thiobacillus sp., and Clavibacter sp.

13. A method of expressing a desired gene within a host cell, comprising introducing into said cell an expression vector as defined in claim 1 containing said desired gene, and culturing said cell under conditions in which said desired gene is expressed.

14. A method of preparing a desired polypeptide product by culturing a host cell containing an expression vector as defined in claim 1 into which a desired gene encoding said desired polypeptide has been introduced, under conditions whereby said polypeptide is expressed, and recovering said desired polypeptide thus produced.

15. A method as claimed in claim 13 or 14, wherein said host cell is selected from the group consisting of Escherichia sp., Salmonella, Klebsiella, Proteus, Yersinia, Azotobacter sp., Pseudomonas sp., Xanthomonas sp., Caulobacter sp., Acinetobacter sp., Aeromonas sp., Agrobacterium sp., Alcaligenes sp., Bordatella sp., Haemophilus Influenzae, *Methylophilus methylotrophus*, Rhizobium sp., Thiobacillus sp., and Clavibacter sp.

* * * * *

SEQUENCE LISTING

<160> NUMBER OF SEQ ID NOS: 5

<210> SEQ ID NO: 1
<211> LENGTH: 43
<212> TYPE: DNA
<213> ORGANISM: Artificial Sequence
<220> FEATURE:
<223> OTHER INFORMATION: A sequence from pJB653ATG

<400> SEQUENCE: 1
ggagtcatga acatgtgaat tcgagctcgg tacccgggga tcc                43

<210> SEQ ID NO: 2
<211> LENGTH: 21
<212> TYPE: DNA
<213> ORGANISM: Artificial Sequence
<220> FEATURE:
<223> OTHER INFORMATION: A primer

<400> SEQUENCE: 2
gatccccatg gaagacgcca a                                       21

<210> SEQ ID NO: 3
<211> LENGTH: 23
<212> TYPE: DNA

-continued

```
<213> ORGANISM: Artificial Sequence
<220> FEATURE:
<223> OTHER INFORMATION: A primer

<400> SEQUENCE: 3
cggaggatcc caatagctaa gaa                                              23

<210> SEQ ID NO: 4
<211> LENGTH: 27
<212> TYPE: DNA
<213> ORGANISM: Artificial Sequence
<220> FEATURE:
<223> OTHER INFORMATION: A primer

<400> SEQUENCE: 4
aggtgaattc acatgttcat gactcca                                          27

<210> SEQ ID NO: 5
<211> LENGTH: 22
<212> TYPE: DNA
<213> ORGANISM: Artificial Sequence
<220> FEATURE:
<223> OTHER INFORMATION: A primer

<400> SEQUENCE: 5
agggctgcag tgtccggttt ga                                               22
```